United States Patent
Reicher et al.

(10) Patent No.: US 9,672,477 B1
(45) Date of Patent: Jun. 6, 2017

(54) EXAM SCHEDULING WITH CUSTOMER CONFIGURED NOTIFICATIONS

(75) Inventors: Murray A. Reicher, Rancho Santa Fe, CA (US); Carol G. Sloyer, La Jolla, CA (US); Tarek El Rashidy, San Diego, CA (US)

(73) Assignee: D.R. SYSTEMS, INC., San Diego, CA (US)

( * ) Notice: Subject to any disclaimer, the term of this patent is extended or adjusted under 35 U.S.C. 154(b) by 1635 days.

(21) Appl. No.: 11/944,000

(22) Filed: Nov. 21, 2007

Related U.S. Application Data

(60) Provisional application No. 60/867,071, filed on Nov. 22, 2006.

(51) Int. Cl.
G06Q 10/00 (2012.01)
G06Q 50/00 (2012.01)

(52) U.S. Cl.
CPC .................... G06Q 10/00 (2013.01)

(58) Field of Classification Search
USPC ......................................... 705/2–3
See application file for complete search history.

(56) References Cited

U.S. PATENT DOCUMENTS

| | | |
|---|---|---|
| 4,672,683 A | 6/1987 | Matsueda |
| 5,123,056 A | 6/1992 | Wilson |
| 5,172,419 A | 12/1992 | Manian |
| 5,179,651 A | 1/1993 | Taaffe et al. |
| 5,431,161 A | 7/1995 | Ryals et al. |
| 5,452,416 A | 9/1995 | Hilton et al. |
| 5,515,375 A | 5/1996 | DeClerck |
| 5,542,003 A | 7/1996 | Wofford |
| 5,734,915 A | 3/1998 | Roewer |
| 5,740,267 A | 4/1998 | Echerer et al. |
| 5,779,634 A | 7/1998 | Ema et al. |
| 5,807,256 A | 9/1998 | Taguchi |
| 5,835,030 A | 11/1998 | Tsutsui et al. |
| 5,852,646 A | 12/1998 | Klotz et al. |
| 5,857,030 A | 1/1999 | Gaborski |
| 5,926,568 A | 7/1999 | Chaney et al. |
| 5,954,650 A | 9/1999 | Saito et al. |
| 5,976,088 A | 11/1999 | Urbano et al. |

(Continued)

FOREIGN PATENT DOCUMENTS

WO    WO 2007/131157    11/2007

OTHER PUBLICATIONS

US 7,801,341, 09/2010, Fram et al. (withdrawn)

(Continued)

*Primary Examiner* — Amber A Misiaszek
(74) *Attorney, Agent, or Firm* — Knobbe, Martens, Olson & Bear LLP

(57) ABSTRACT

An exam scheduling device comprises a notification module configured to determine notifications for display to a scheduler in the process of scheduling an exam for a patient. The notifications presented to a particular scheduler may be selected based on one or more exam parameters associated with a patient, for example. Thus, only those notifications that are relevant to the exam parameters associated with a particular patient's exam are presented to the scheduler, and the scheduler is required to respond to only those notifications that a scheduling administrator has determined require a response.

5 Claims, 15 Drawing Sheets

(56) References Cited

U.S. PATENT DOCUMENTS

| | | |
|---|---|---|
| 5,986,662 A | 11/1999 | Argiro et al. |
| 5,987,345 A | 11/1999 | Engelmann et al. |
| 5,995,644 A | 11/1999 | Lai et al. |
| 6,008,813 A | 12/1999 | Lauer et al. |
| 6,115,486 A | 9/2000 | Cantoni |
| 6,128,002 A | 10/2000 | Leiper |
| 6,130,671 A | 10/2000 | Argiro |
| 6,151,581 A * | 11/2000 | Kraftson ............ G06F 19/327 705/2 |
| 6,175,643 B1 | 1/2001 | Lai et al. |
| 6,177,937 B1 | 1/2001 | Stockham et al. |
| 6,185,320 B1 | 2/2001 | Bick et al. |
| 6,211,884 B1 | 4/2001 | Knittel et al. |
| 6,219,059 B1 | 4/2001 | Argiro |
| 6,219,061 B1 | 4/2001 | Lauer et al. |
| 6,243,095 B1 | 6/2001 | Shile et al. |
| 6,243,098 B1 | 6/2001 | Lauer et al. |
| 6,262,740 B1 | 7/2001 | Lauer et al. |
| 6,266,733 B1 | 7/2001 | Knittel et al. |
| 6,269,379 B1 | 7/2001 | Hiyama et al. |
| 6,297,799 B1 | 10/2001 | Knittel et al. |
| 6,304,667 B1 | 10/2001 | Reitano |
| 6,310,620 B1 | 10/2001 | Lauer et al. |
| 6,313,841 B1 | 11/2001 | Ogata et al. |
| 6,342,885 B1 | 1/2002 | Knittel et al. |
| 6,347,329 B1 | 2/2002 | Evans |
| 6,351,547 B1 | 2/2002 | Johnson et al. |
| 6,356,265 B1 | 3/2002 | Knittel et al. |
| 6,369,816 B1 | 4/2002 | Knittel et al. |
| 6,383,135 B1 | 5/2002 | Chikovani et al. |
| 6,388,687 B1 | 5/2002 | Brackett et al. |
| 6,404,429 B1 | 6/2002 | Knittel |
| 6,407,737 B1 | 6/2002 | Zhao et al. |
| 6,411,296 B1 | 6/2002 | Knittel et al. |
| 6,421,057 B1 | 7/2002 | Lauer et al. |
| 6,424,346 B1 | 7/2002 | Correll et al. |
| 6,424,996 B1 | 7/2002 | Killcommons et al. |
| 6,426,749 B1 | 7/2002 | Knittel et al. |
| 6,438,533 B1 | 8/2002 | Spackman et al. |
| 6,463,169 B1 | 10/2002 | Ino et al. |
| 6,476,810 B1 | 11/2002 | Simha et al. |
| 6,512,517 B1 | 1/2003 | Knittel et al. |
| 6,532,299 B1 | 3/2003 | Sachdeva et al. |
| 6,532,311 B1 | 3/2003 | Pritt |
| 6,556,695 B1 | 4/2003 | Packer et al. |
| 6,556,724 B1 | 4/2003 | Chang et al. |
| 6,563,950 B1 | 5/2003 | Wiskott et al. |
| 6,574,629 B1 | 6/2003 | Cooke et al. |
| 6,577,753 B2 | 6/2003 | Ogawa |
| 6,603,494 B1 | 8/2003 | Banks et al. |
| 6,606,171 B1 | 8/2003 | Renk et al. |
| 6,614,447 B1 | 9/2003 | Bhatia et al. |
| 6,618,060 B1 | 9/2003 | Brackett |
| 6,621,918 B1 | 9/2003 | Hu et al. |
| 6,630,937 B2 | 10/2003 | Kallergi et al. |
| 6,650,766 B1 | 11/2003 | Rogers |
| 6,654,012 B1 | 11/2003 | Lauer et al. |
| 6,678,764 B2 | 1/2004 | Parvulescu et al. |
| 6,680,735 B1 | 1/2004 | Seiler et al. |
| 6,683,933 B2 | 1/2004 | Saito et al. |
| 6,697,067 B1 | 2/2004 | Callahan et al. |
| 6,697,506 B1 | 2/2004 | Qian et al. |
| 6,734,880 B2 | 5/2004 | Chang et al. |
| 6,760,755 B1 | 7/2004 | Brackett |
| 6,775,402 B2 | 8/2004 | Bacus et al. |
| 6,778,689 B1 | 8/2004 | Aksit et al. |
| 6,820,093 B2 | 11/2004 | de la Huerga |
| 6,820,100 B2 | 11/2004 | Funahashi |
| 6,826,297 B2 | 11/2004 | Saito et al. |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,917,696 B2 | 7/2005 | Soenksen |
| 6,988,075 B1 | 1/2006 | Hacker |
| 6,996,205 B2 | 2/2006 | Capolunghi et al. |
| 7,016,952 B2 | 3/2006 | Mullen et al. |
| 7,022,073 B2 | 4/2006 | Fan et al. |
| 7,027,633 B2 | 4/2006 | Foran et al. |
| 7,031,504 B1 | 4/2006 | Argiro et al. |
| 7,031,846 B2 | 4/2006 | Kaushikkar et al. |
| 7,039,723 B2 | 5/2006 | Hu et al. |
| 7,043,474 B2 | 5/2006 | Mojsilovic |
| 7,050,620 B2 | 5/2006 | Heckman |
| 7,054,473 B1 | 5/2006 | Roehrig et al. |
| 7,058,901 B1 | 6/2006 | Hafey et al. |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,113,186 B2 | 9/2006 | Kim et al. |
| 7,136,064 B2 | 11/2006 | Zuiderveld |
| 7,139,416 B2 | 11/2006 | Vuylsteke |
| 7,149,334 B2 | 12/2006 | Dehmeshki |
| 7,155,043 B2 | 12/2006 | Daw |
| 7,162,623 B2 | 1/2007 | Yngvesson |
| 7,170,532 B2 | 1/2007 | Sako |
| 7,174,054 B2 | 2/2007 | Manber et al. |
| 7,209,149 B2 | 4/2007 | Jogo |
| 7,209,578 B2 | 4/2007 | Saito et al. |
| 7,212,661 B2 | 5/2007 | Samara et al. |
| 7,218,763 B2 | 5/2007 | Belykh et al. |
| 7,224,852 B2 | 5/2007 | Lipton et al. |
| 7,236,558 B2 | 6/2007 | Saito et al. |
| 7,260,249 B2 | 8/2007 | Smith |
| 7,263,710 B1 | 8/2007 | Hummell et al. |
| 7,272,610 B2 | 9/2007 | Torres |
| 7,346,199 B2 | 3/2008 | Pfaff |
| 7,366,992 B2 | 4/2008 | Thomas, III |
| 7,412,111 B2 | 8/2008 | Battle et al. |
| 7,450,747 B2 | 11/2008 | Jabri et al. |
| 7,492,970 B2 | 2/2009 | Saito et al. |
| 7,505,782 B2 | 3/2009 | Chu |
| 7,525,554 B2 | 4/2009 | Morita et al. |
| 7,526,114 B2 | 4/2009 | Seul et al. |
| 7,526,132 B2 | 4/2009 | Koenig |
| 7,545,965 B2 | 6/2009 | Suzuki et al. |
| 7,574,029 B2 | 8/2009 | Peterson et al. |
| 7,583,861 B2 | 9/2009 | Hanna et al. |
| 7,590,272 B2 | 9/2009 | Brejl et al. |
| 7,613,335 B2 | 11/2009 | McLennan et al. |
| 7,634,121 B2 | 12/2009 | Novatzky et al. |
| 7,636,413 B2 | 12/2009 | Toth |
| 7,639,879 B2 | 12/2009 | Goto et al. |
| 7,656,543 B2 | 2/2010 | Atkins |
| 7,660,481 B2 | 2/2010 | Schaap et al. |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,835,560 B2 | 11/2010 | Vining et al. |
| 7,885,440 B2 | 2/2011 | Fram et al. |
| 7,885,828 B2 | 2/2011 | Glaser-Seidnitzer et al. |
| 7,899,514 B1 | 3/2011 | Kirkland |
| 7,920,152 B2 | 4/2011 | Fram et al. |
| 7,953,614 B1 | 5/2011 | Reicher |
| 7,970,188 B2 | 6/2011 | Mahesh et al. |
| 7,970,625 B2 | 6/2011 | Reicher et al. |
| 7,991,210 B2 | 8/2011 | Peterson et al. |
| 7,992,100 B2 | 8/2011 | Lundstrom et al. |
| 8,019,138 B2 | 9/2011 | Reicher et al. |
| 8,046,044 B2 | 10/2011 | Stazzone et al. |
| 8,050,938 B1 | 11/2011 | Green, Jr. et al. |
| 8,065,166 B2 | 11/2011 | Maresh et al. |
| 8,073,225 B2 | 12/2011 | Hagen et al. |
| 8,094,901 B1 | 1/2012 | Reicher et al. |
| 8,150,708 B2 | 4/2012 | Kotula et al. |
| 8,214,756 B2 | 7/2012 | Salazar-Ferrer et al. |

(56) References Cited

U.S. PATENT DOCUMENTS

| | | |
|---|---|---|
| 8,217,966 B2 | 7/2012 | Fram et al. |
| 8,244,014 B2 | 8/2012 | Murray et al. |
| 8,249,687 B2 | 8/2012 | Peterson et al. |
| 8,292,811 B2 | 10/2012 | Relkuntwar et al. |
| 8,370,293 B2 | 2/2013 | Iwase et al. |
| 8,379,051 B2 | 2/2013 | Brown |
| 8,380,533 B2 | 2/2013 | Reicher et al. |
| 8,391,643 B2 | 3/2013 | Melbourne et al. |
| 8,406,491 B2 | 3/2013 | Gee et al. |
| 8,457,990 B1 | 6/2013 | Reicher et al. |
| 8,554,576 B1 | 10/2013 | Reicher et al. |
| 8,560,050 B2 | 10/2013 | Martin et al. |
| 8,610,746 B2 | 12/2013 | Fram et al. |
| 8,626,527 B1 | 1/2014 | Reicher et al. |
| 8,693,757 B2 | 4/2014 | Gundel |
| 8,712,120 B1 | 4/2014 | Reicher et al. |
| 8,731,259 B2 | 5/2014 | Reicher et al. |
| 8,751,268 B1 | 6/2014 | Reicher et al. |
| 8,797,350 B2 | 8/2014 | Fram |
| 8,879,807 B2 | 11/2014 | Fram et al. |
| 8,913,808 B2 | 12/2014 | Reicher et al. |
| 9,042,617 B1 | 5/2015 | Reicher et al. |
| 9,075,899 B1 | 7/2015 | Reicher |
| 9,092,551 B1 | 7/2015 | Reicher |
| 9,092,727 B1 | 7/2015 | Reicher |
| 9,324,188 B1 | 4/2016 | Fram et al. |
| 9,386,084 B1 | 7/2016 | Reicher et al. |
| 9,471,210 B1 | 10/2016 | Fram et al. |
| 9,495,604 B1 | 11/2016 | Fram |
| 9,501,617 B1 | 11/2016 | Reicher et al. |
| 9,501,627 B2 | 11/2016 | Reicher et al. |
| 9,501,863 B2 | 11/2016 | Fram et al. |
| 9,542,082 B1 | 1/2017 | Reicher et al. |
| 2001/0016822 A1 | 8/2001 | Bessette |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0070970 A1 | 6/2002 | Wood et al. |
| 2002/0073429 A1 | 6/2002 | Beane et al. |
| 2002/0090119 A1 | 7/2002 | Saito et al. |
| 2002/0090124 A1 | 7/2002 | Soubelet et al. |
| 2002/0091659 A1 | 7/2002 | Beaulieu et al. |
| 2002/0103673 A1* | 8/2002 | Atwood .................. 705/2 |
| 2002/0103827 A1 | 8/2002 | Sesek |
| 2002/0110285 A1 | 8/2002 | Wang et al. |
| 2002/0144697 A1 | 10/2002 | Betz |
| 2002/0172408 A1 | 11/2002 | Saito et al. |
| 2002/0172409 A1 | 11/2002 | Saito et al. |
| 2002/0180883 A1 | 12/2002 | Tomizawa et al. |
| 2002/0186820 A1 | 12/2002 | Saito et al. |
| 2002/0190984 A1 | 12/2002 | Seiler et al. |
| 2003/0005464 A1 | 1/2003 | Gropper et al. |
| 2003/0013951 A1 | 1/2003 | Stefanescu |
| 2003/0016850 A1 | 1/2003 | Kaufman et al. |
| 2003/0028402 A1 | 2/2003 | Ulrich et al. |
| 2003/0034973 A1 | 2/2003 | Zuiderveld |
| 2003/0037054 A1 | 2/2003 | Dutta et al. |
| 2003/0055896 A1 | 3/2003 | Hu et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0130973 A1* | 7/2003 | Sumner, II .......... G06F 19/3437 706/45 |
| 2003/0140141 A1 | 7/2003 | Mullen et al. |
| 2003/0156745 A1 | 8/2003 | Saito et al. |
| 2003/0160095 A1 | 8/2003 | Segal |
| 2003/0164860 A1 | 9/2003 | Shen et al. |
| 2003/0184778 A1 | 10/2003 | Chiba |
| 2003/0187689 A1 | 10/2003 | Barnes et al. |
| 2003/0190062 A1 | 10/2003 | Noro et al. |
| 2003/0204420 A1 | 10/2003 | Wilkes et al. |
| 2003/0215122 A1 | 11/2003 | Tanaka |
| 2004/0015703 A1 | 1/2004 | Madison et al. |
| 2004/0024303 A1 | 2/2004 | Banks et al. |
| 2004/0086163 A1 | 5/2004 | Moriyama et al. |
| 2004/0088192 A1 | 5/2004 | Schmidt et al. |
| 2004/0105030 A1 | 6/2004 | Yamane |
| 2004/0105574 A1 | 6/2004 | Pfaff |
| 2004/0114714 A1 | 6/2004 | Minyard et al. |
| 2004/0122705 A1 | 6/2004 | Sabol et al. |
| 2004/0143582 A1 | 7/2004 | Vu |
| 2004/0161139 A1 | 8/2004 | Samara et al. |
| 2004/0161164 A1 | 8/2004 | Dewaele |
| 2004/0165791 A1 | 8/2004 | Kaltanji |
| 2004/0172306 A1 | 9/2004 | Wohl et al. |
| 2004/0174429 A1 | 9/2004 | Chu |
| 2004/0190780 A1 | 9/2004 | Shiibashi et al. |
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2004/0255252 A1 | 12/2004 | Rodriguez et al. |
| 2005/0010531 A1 | 1/2005 | Kushalnagar et al. |
| 2005/0027569 A1 | 2/2005 | Gollogly et al. |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074150 A1 | 4/2005 | Bruss |
| 2005/0074157 A1 | 4/2005 | Thomas, III |
| 2005/0075544 A1 | 4/2005 | Shapiro et al. |
| 2005/0088534 A1 | 4/2005 | Shen et al. |
| 2005/0107689 A1 | 5/2005 | Sasano |
| 2005/0108058 A1 | 5/2005 | Weidner et al. |
| 2005/0110791 A1 | 5/2005 | Krishnamoorthy et al. |
| 2005/0113681 A1 | 5/2005 | DeFreitas et al. |
| 2005/0114178 A1 | 5/2005 | Krishnamurthy et al. |
| 2005/0114179 A1 | 5/2005 | Brackett et al. |
| 2005/0114283 A1 | 5/2005 | Pearson et al. |
| 2005/0143654 A1 | 6/2005 | Zuiderveld et al. |
| 2005/0171818 A1* | 8/2005 | McLaughlin .......... G06Q 10/10 705/3 |
| 2005/0184988 A1 | 8/2005 | Yanof et al. |
| 2005/0197860 A1 | 9/2005 | Joffe et al. |
| 2005/0238218 A1 | 10/2005 | Nakamura |
| 2005/0244041 A1 | 11/2005 | Tecotzky et al. |
| 2005/0251013 A1 | 11/2005 | Krishnan |
| 2005/0254729 A1 | 11/2005 | Saito et al. |
| 2005/0273009 A1 | 12/2005 | Deischinger et al. |
| 2006/0008181 A1 | 1/2006 | Takekoshi |
| 2006/0031097 A1* | 2/2006 | Lipscher et al. ................. 705/2 |
| 2006/0050152 A1 | 3/2006 | Rai et al. |
| 2006/0058603 A1 | 3/2006 | Dave et al. |
| 2006/0093198 A1 | 5/2006 | Fram et al. |
| 2006/0093199 A1 | 5/2006 | Fram et al. |
| 2006/0095423 A1 | 5/2006 | Reicher et al. |
| 2006/0095426 A1 | 5/2006 | Takachio et al. |
| 2006/0106642 A1 | 5/2006 | Reicher et al. |
| 2006/0111941 A1 | 5/2006 | Blom |
| 2006/0122482 A1 | 6/2006 | Mariotti et al. |
| 2006/0171574 A1 | 8/2006 | DelMonego et al. |
| 2006/0181548 A1 | 8/2006 | Hafey |
| 2006/0188134 A1 | 8/2006 | Quist |
| 2006/0230072 A1 | 10/2006 | Partovi et al. |
| 2006/0241979 A1 | 10/2006 | Sato et al. |
| 2006/0267976 A1 | 11/2006 | Saito et al. |
| 2006/0276708 A1 | 12/2006 | Peterson et al. |
| 2006/0277075 A1 | 12/2006 | Salwan |
| 2006/0282408 A1 | 12/2006 | Wisely et al. |
| 2007/0009078 A1 | 1/2007 | Saito et al. |
| 2007/0021977 A1 | 1/2007 | Elsholz |
| 2007/0050701 A1 | 3/2007 | El Emam et al. |
| 2007/0055550 A1 | 3/2007 | Courtney et al. |
| 2007/0064984 A1 | 3/2007 | Vassa et al. |
| 2007/0067124 A1 | 3/2007 | Kimpe et al. |
| 2007/0073556 A1 | 3/2007 | Lau et al. |
| 2007/0106535 A1 | 5/2007 | Matsunaga |
| 2007/0106633 A1 | 5/2007 | Reiner |
| 2007/0109299 A1 | 5/2007 | Peterson |
| 2007/0109402 A1 | 5/2007 | Niwa |

(56) References Cited

U.S. PATENT DOCUMENTS

| | | |
|---|---|---|
| 2007/0110294 A1 | 5/2007 | Schaap et al. |
| 2007/0116345 A1 | 5/2007 | Peterson et al. |
| 2007/0116346 A1 | 5/2007 | Peterson et al. |
| 2007/0122016 A1 | 5/2007 | Brejl et al. |
| 2007/0124541 A1 | 5/2007 | Lang et al. |
| 2007/0140536 A1 | 6/2007 | Sehnert |
| 2007/0159962 A1 | 7/2007 | Mathavu et al. |
| 2007/0162308 A1 | 7/2007 | Peters |
| 2007/0165917 A1 | 7/2007 | Cao et al. |
| 2007/0174079 A1 | 7/2007 | Kraus |
| 2007/0192138 A1 | 8/2007 | Saito et al. |
| 2007/0192140 A1 | 8/2007 | Gropper |
| 2007/0237380 A1 | 10/2007 | Iwase et al. |
| 2007/0239481 A1 | 10/2007 | DiSilvestro et al. |
| 2008/0016111 A1 | 1/2008 | Keen |
| 2008/0021877 A1 | 1/2008 | Saito et al. |
| 2008/0059245 A1 | 3/2008 | Sakaida et al. |
| 2008/0100612 A1 | 5/2008 | Dastmalchi et al. |
| 2008/0103828 A1 | 5/2008 | Squilla et al. |
| 2008/0125846 A1 | 5/2008 | Battle et al. |
| 2008/0126982 A1 | 5/2008 | Sadikali et al. |
| 2008/0136838 A1 | 6/2008 | Goede et al. |
| 2008/0275913 A1 | 11/2008 | van Arragon et al. |
| 2008/0279439 A1 | 11/2008 | Minyard et al. |
| 2008/0300484 A1 | 12/2008 | Wang et al. |
| 2009/0005668 A1 | 1/2009 | West et al. |
| 2009/0022375 A1 | 1/2009 | Fidrich |
| 2009/0028410 A1 | 1/2009 | Shimazaki |
| 2009/0080719 A1 | 3/2009 | Watt |
| 2009/0091566 A1 | 4/2009 | Turney et al. |
| 2009/0123052 A1 | 5/2009 | Ruth et al. |
| 2009/0129643 A1 | 5/2009 | Natanzon et al. |
| 2009/0132586 A1 | 5/2009 | Napora et al. |
| 2009/0150481 A1 | 6/2009 | Garcia et al. |
| 2009/0182577 A1 | 7/2009 | Squilla et al. |
| 2009/0198514 A1 | 8/2009 | Rhodes |
| 2009/0213034 A1 | 8/2009 | Wu et al. |
| 2009/0248442 A1 | 10/2009 | Pacheco et al. |
| 2009/0268986 A1 | 10/2009 | Holstein et al. |
| 2009/0326373 A1 | 12/2009 | Boese et al. |
| 2010/0053353 A1 | 3/2010 | Hunter et al. |
| 2010/0086182 A1 | 4/2010 | Luo et al. |
| 2010/0131887 A1 | 5/2010 | Salazar-Ferrer et al. |
| 2010/0138239 A1 | 6/2010 | Reicher et al. |
| 2010/0198608 A1 | 8/2010 | Kaboff et al. |
| 2010/0201714 A1 | 8/2010 | Reicher |
| 2010/0211409 A1 | 8/2010 | Kotula et al. |
| 2010/0246981 A1 | 9/2010 | Hu et al. |
| 2010/0299157 A1 | 11/2010 | Fram et al. |
| 2011/0016430 A1 | 1/2011 | Fram |
| 2011/0110572 A1 | 5/2011 | Guehring et al. |
| 2011/0267339 A1 | 11/2011 | Fram |
| 2011/0293162 A1 | 12/2011 | Pajeau |
| 2011/0316873 A1 | 12/2011 | Reicher |
| 2012/0070048 A1 | 3/2012 | Van Den Brink |
| 2012/0130729 A1 | 5/2012 | Raizada et al. |
| 2012/0136794 A1 | 5/2012 | Kushalnagar et al. |
| 2012/0163684 A1 | 6/2012 | Natanzon et al. |
| 2012/0194540 A1 | 8/2012 | Reicher |
| 2012/0284657 A1 | 11/2012 | Hafey et al. |
| 2013/0070998 A1 | 3/2013 | Shibata |
| 2013/0076681 A1 | 3/2013 | Sirpal et al. |
| 2013/0083023 A1 | 4/2013 | Fram et al. |
| 2013/0159019 A1 | 6/2013 | Reicher et al. |
| 2013/0297331 A1 | 11/2013 | Zuehlsdorff et al. |
| 2014/0022194 A1 | 1/2014 | Ito |
| 2014/0142983 A1 | 5/2014 | Backhaus et al. |
| 2015/0160848 A1 | 6/2015 | Gkanatsios et al. |
| 2016/0034110 A1 | 2/2016 | Edwards |
| 2016/0335395 A1 | 11/2016 | Wu et al. |
| 2017/0038951 A1 | 2/2017 | Reicher |
| 2017/0039321 A1 | 2/2017 | Reicher |
| 2017/0039322 A1 | 2/2017 | Reicher |
| 2017/0039350 A1 | 2/2017 | Reicher |
| 2017/0039705 A1 | 2/2017 | Fram |
| 2017/0046014 A1 | 2/2017 | Fram |
| 2017/0046483 A1 | 2/2017 | Reicher |
| 2017/0046485 A1 | 2/2017 | Reicher |
| 2017/0046495 A1 | 2/2017 | Fram |
| 2017/0046870 A1 | 2/2017 | Fram |
| 2017/0053404 A1 | 2/2017 | Reicher |

OTHER PUBLICATIONS

US 8,208,705, 06/2012, Reicher et al. (withdrawn)

Sandberg, et al., "Automatic detection and notification of "wrong patient-wrong location" errors in the operating room", Surgical Innovation, vol. 12, No. 3, Sep. 2005, pp. 253-260.*

Crowley, Rebecca et al., *Development of Visual Diagnostic Expertise in Pathology: an Information-processing Study*, Jan. 2003, Journal of the American medical Informatics Association, vol. 10, No. 1, pp. 39-51.

Non-Final Office Action dated Aug. 28, 2007 in U.S. Appl. No. 11/179,384.

Final Office Action dated Jun. 26, 2008 in U.S. Appl. No. 11/179,384.

Non-Final Office Action dated Dec. 29, 2008 in U.S. Appl. No. 11/179,384.

Final Office Action dated Jul. 24, 2009, in U.S. Appl. No. 11/179,384.

Notice of Allowance dated Nov. 3, 2009, in U.S. Appl. No. 11/179,384.

Non-Final Office Action dated Oct. 1, 2009, in U.S. Appl. No. 11/268,261.

Notice of Allowance dated Feb. 2, 2010, in U.S. Appl. No. 11/268,261.

Non-Final Office Action dated May 13, 2009, in U.S. Appl. No. 11/265,979.

Final Office Action dated Dec. 22, 2009 in U.S. Appl. No. 11/265,979.

Non-Final Office Action dated Aug. 24, 2009 in U.S. Appl. No. 11/268,262.

Non-Final Office Action dated Apr. 16, 2010 in U.S. Appl. No. 11/268,262.

Non-Final Office Action dated Jul. 27, 2009 in U.S. Appl. No. 11/265,978.

Notice of Allowance dated Nov. 19, 2009 in U.S. Appl. No. 11/265,978.

Notice of Allowance dated Apr. 19, 2010 in U.S. Appl. No. 11/265,978.

Supplemental Notice of Allowance dated May 3, 2010 in U.S. Appl. No. 11/265,978.

Non-Final Office Action dated Apr. 14, 2010 in U.S. Appl. No. 11/944,027.

Non-Final Office Action dated May 26, 2010 in U.S. Appl. No. 11/942,673.

Non-Final Office Action dated Aug. 18, 2010 in U.S. Appl. No. 12/702,976.

Interview Summary dated May 14, 2010, in U.S. Appl. No. 11/268,261.

Non-Final Office Action dated Jul. 8, 2010 in U.S. Appl. No. 11/265,979.

Interview Summary dated Mar. 4, 2010 in U.S. Appl. No. 11/265,979.

Interview Summary dated Nov. 24, 2009 in U.S. Appl. No. 11/268,262.

Interview Summary dated May 12, 2010 in U.S. Appl. No. 11/268,262.

Supplemental Notice of Allowance dated Aug. 3, 2010 in U.S. Appl. No. 11/265,978.

Interview Summary dated Jul. 26, 2010 in U.S. Appl. No. 11/942,673.

NonFinal Office Action dated Sep. 16, 2010 in U.S. Appl. No. 11/942,687.

Interview Summary dated May 13, 2010 in U.S. Appl. No. 11/944,027.

Interview Summary dated Dec. 1, 2010, 2010 in U.S. Appl. No. 12/702,976.

(56) References Cited

OTHER PUBLICATIONS

Notice of Allowance dated Oct. 8, 2010, in U.S. Appl. No. 11/268,261.
Notice of Allowance dated Dec. 3, 2010, in U.S. Appl. No. 11/268,261.
Notice of Allowance dated Jan. 6, 2011, in U.S. Appl. No. 11/268,261.
Interview Summary dated Nov. 16, 2010 in U.S. Appl. No. 11/265,979.
Final Office Action dated Dec. 23, 2010 in U.S. Appl. No. 11/265,979.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Final Office Action dated Nov. 26, 2010 in U.S. Appl. No. 11/942,673.
Interview Summary dated Dec. 3, 2010 in U.S. Appl. No. 11/942,687.
Final Office Action dated Dec. 23, 2010 in U.S. Appl. No. 11/944,027.
Final Office Action dated Feb. 17, 2011 in U.S. Appl. No. 12/702,976.
Interview Summary dated May 31, 2011 in U.S. Appl. No. 12/702,976.
Notice of Allowance dated Jul. 20, 2011 in U.S. Appl. No. 12/702,976.
Office Action dated May 16, 2011, in U.S. Appl. No. 12/857,915.
Interview Summary dated Sep. 6, 2011, in U.S. Appl. No. 12/857,915.
Interview Summary dated Mar. 17, 2011 in U.S. Appl. No. 11/265,979.
Notice of Allowance dated May 26, 2011 in U.S. Appl. No. 11/265,979.
Notice of Allowance dated Feb. 25, 2011 in U.S. Appl. No. 11/268,262.
Non-Final Office Action dated May 5, 2011 in U.S. Appl. No. 12/870,645.
Interview Summary dated Mar. 2, 2011 in U.S. Appl. No. 11/942,674.
Notice of Allowance, dated Apr. 1, 2011 in U.S. Appl. No. 11/942,674.
Final Office Action, dated Apr. 5, 2011 in U.S. Appl. No. 11/942,687.
Interview Summary dated Mar. 31, 2011 in U.S. Appl. No. 11/944,027.
Office Action dated Dec. 1, 2011, in U.S. Appl. No. 13/228,349.
Notice of Allowance dated Feb. 6, 2012, in U.S. Appl. No. 13/228,349.
Notice of Allowance dated Jul. 20, 2012, in U.S. Appl. No. 13/228,349.
Final Office Action dated Dec. 15, 2011, in U.S. Appl. No. 12/857,915.
Office Action dated Jun. 12, 2012, in U.S. Appl. No. 12/857,915.
Office Action dated Jun. 8, 2012 in U.S. Appl. No. 13/171,081.
Interview Summary dated Jul. 31, 2012 in U.S. Appl. No. 13/171,081.
Non-Final Office Action dated Jan. 11, 2012 in U.S. Appl. No. 13/079,597.
Notice of Allowance dated Apr. 25, 2012, in U.S. Appl. No. 13/079,597.
Non Final Office Action Dated Nov. 10, 2011 in U.S. Appl. No. 13/118,085.
Interview Summary, dated Feb. 17, 2012 in U.S. Appl. No. 13/118,085.
Final Office Action, dated Apr. 13, 2012 in U.S. Appl. No. 13/118,085.
Office Action dated Apr. 19, 2012 in U.S. Appl. No. 11/944,027.
Interview Summary dated Jun. 28, 2012 in U.S. Appl. No. 11/944,027.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Mendelson, et al., "Informatics in Radiology—Image Exchange: IHE and the Evolution of Image Sharing," RadioGraphics, Nov.-Dec. 2008, vol. 28, No. 7.
U.S. Appl. No. 14/081,225, Systems and Methods for Viewing Medical 3D Imaging Volumes, filed Nov. 15, 2013.
U.S. Appl. No. 14/244,431, Systems and Methods for Matching, Naming, and Displaying Medical Images, filed Apr. 3, 2014.
U.S. Appl. No. 13/768,765, System and Method of Providing Dynamic and Customizable Medical Examination Forms, filed Feb. 15, 2013.
U.S. Appl. No. 15/163,600, Rules-Based Approach to Transferring and/or Viewing Medical Images, filed May 24, 2016.
U.S. Appl. No. 15/140,351, Database Systems and Interactive User Interfaces for Dynamic Interaction With, and Review of, Digital Medical Image Da, filed Apr. 27, 2016.
U.S. Appl. No. 15/140,348, Database Systems and Interactive User Interfaces for Dynamic Interaction With, and Indications of, Digital Medical Image Data, filed Apr. 27, 2016.
AGFA HealthCare, color brochure "IMPAX 6: Digital Image and Information Management," © 2012 Agfa HealthCare N.V. Downloaded from http://www.agfahealthcare.com/global/en/he/library/libraryopen?ID-32882925. Accessed on Feb. 9, 2015.
AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
ASPYRA's Imaging Solutions, 3 page color print out. Accessed at http://www.aspyra.com/imaging-solutions. Accessed on Feb. 9, 2015.
Avreo, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 Dec. 2012). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 May 2014). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332 _10_v3). Downloaded from http://www.cerner.com/uploadedFiles/Clinical_Imaging.pdf. Accessed on Feb. 9, 2015.

(56) References Cited

OTHER PUBLICATIONS

CoActiv, Exam-Pacs, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015. [submitted in 2 parts].
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015. [submitted in 2 parts].
Erickson, et al.: "Effect of Automated Image Registration on Radiologist Interpretation," Journal of Digital Imaging, vol. 20, No. 2 Jun. 2007; pp. 105-113.
Erickson, et al.: "Image Registration Improves Confidence and Accuracy of Image Interpretation," Special Issue-Imaging Informatics, Cancer Informatics 2007: 1 19-24.
Fujifilm Medical Systems, Synapse® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
Fujifilm Medical Systems, Synapse® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
Fujifilm Medical Systems, Synapse® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See The Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incorporated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incorporated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Rosset et al.: "OsiriX: An Open-Source Software for Navigating in Multidimensional DICOM Images," Journal of digital Imaging, Sep. 2004, pp. 205-216.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
Schellingerhout, Dawid, MD, et al.: "Coregistration of Head CT Comparison Studies: Assessment of Clinical Utility," Acad Radiol 2003; 10:242-248.
ScImage, Cardiology PACS, in 8 color page printout. Accessed at http://www.scimage.com/solutions/clinical-solutions/cardiology. Accessed on Feb. 9 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.

(56) References Cited

OTHER PUBLICATIONS

Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra Vision, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Ivetic, D., and Dragan, D., Medical Image on the Go!, 2009, J Med Syst, vol. 35, pp. 499-516.
Tahmoush, D. and Samet, H., A New Database for Medical Images and Information, 2007, Medical Imaging 2007; PACS and Imaging Informatics, vol. 6516. pp. 1-9.
Office Action dated Dec. 11, 2013, in U.S. Appl. No. 13/477,853.
Interview Summary dated Mar. 14, 2014, in U.S. Appl. No. 13/477,853.
Final Office Action dated Jun. 13, 2014, in U.S. Appl. No. 13/477,853.
Notice of Allowance dated Aug. 15, 2014, in U.S. Appl. No. 13/477,853.
Interview Summary dated Jan. 25, 2010, in U.S. Appl. No. 11/268,261.
Notice of Allowance dated May 17, 2010, in U.S. Appl. No. 11/268,261.
Supplemental Notice of Allowance dated Aug. 6, 2010, in U.S. Appl. No. 11/268,261.
Office Action dated Aug. 23, 2013, in U.S. Appl. No. 12/857,915.
Interview Summary dated Feb. 4, 2014, in U.S. Appl. No. 12/857,915.
Notice of Allowance dated Jul. 3, 2014, in U.S. Appl. No. 12/857,915.
"Corrected" Notice of Allowance dated Aug. 15, 2014, in U.S. Appl. No. 12/857,915.
Non-Final Office Action dated Jan. 20, 2016, in U.S. Appl. No. 14/502,055.
Interview Summary dated Apr. 14, 2016, in U.S. Appl. No. 14/502,055.
Notice of Allowance dated Jun. 2, 2016, in U.S. Appl. No. 14/502,055.
Notice of Corrected Allowability dated Jul. 14, 2016, in U.S. Appl. No. 14/502,055.
Notice of Corrected Allowability dated Sep. 19, 2016, in U.S. Appl. No. 14/502,055.
Final Office Action dated Oct. 12, 2012 in U.S. Appl. No. 13/171,081.
Interview Summary dated Nov. 6, 2012 in U.S. Appl. No. 13/171,081.
Notice of Allowance, dated Sep. 4, 2013, in U.S. Appl. No. 13/171,081.
Office Action dated Mar. 3, 2015 in U.S. Appl. No. 14/095,123.
Interview Summary dated May 1, 2015 in U.S. Appl. No. 14/095,123.
Final Office Action dated Jul. 23, 2015 in U.S. Appl. No. 14/095,123.
Interview Summary dated Aug. 27, 2015 in U.S. Appl. No. 14/095,123.
Office Action dated Feb. 23, 2016 in U.S. Appl. No. 14/095,123.
Final Office Action dated Jul. 20, 2016 in U.S. Appl. No. 14/095,123.
Non-Final Office Action dated Apr. 4, 2013 in U.S. Appl. No. 13/535,758.
Notice of Allowance, dated Aug. 23, 2013 in U.S. Appl. No. 13/535,758.
Corrected Notice of Allowance dated Jun. 27, 2016, in U.S. Appl. No. 14/502,055.
Office Action dated Mar. 10, 2016 in U.S. Appl. No. 14/081,225.
Notice of Allowance dated Sep. 2, 2016 in U.S. Appl. No. 14/081,225.
Non-Final Office Action dated May 31, 2013, in U.S. Appl. No. 13/345,606.
Interview Summary dated Aug. 15, 2013, in U.S. Appl. No. 13/345,606.
Notice of Allowance, dated Jan. 9, 2014 in U.S. Appl. No. 13/345,606.
Non-Final Office Action dated Mar. 18, 2016 in U.S. Appl. No. 14/244,431.
Interview Summary dated Jun. 17, 2016 in U.S. Appl. No. 14/244,431.
Notice of Allowance dated Aug. 18, 2016 in U.S. Appl. No. 14/244,431.
Notice of Allowance, dated Feb. 6, 2013, in U.S. Appl. No. 13/118,085.
Non Final Office Action dated Aug. 23, 2013 in U.S. Appl. No. 13/907,128.
Final Office Action dated Oct. 9, 2013 in U.S. Appl. No. 13/907,128.
Interview Summary dated Nov. 22, 2013 in U.S. Appl. No. 13/907,128.
Notice of Allowance dated Jan. 31, 2014 in U.S. Appl. No. 13/907,128.
Office Action, dated Dec. 29, 2014 in U.S. Appl. No. 14/298,806.
Interview Summary, dated Mar. 2, 2015 in U.S. Appl. No. 14/298,806.
Final Office Action, dated Jun. 17, 2015 in U.S. Appl. No. 14/298,806.
Office Action, dated Feb. 16, 2016 in U.S. Appl. No. 14/298,806.
Final Office Action, dated Jul. 21, 2016 in U.S. Appl. No. 14/298,806.
Office Action, dated Mar. 13, 2014 in U.S. Appl. No. 11/942,687.
Interview Summary, dated Jun. 17, 2014 in U.S. Appl. No. 11/942,687.
Office Action, dated Jul. 18, 2014 in U.S. Appl. No. 11/942,687.
Final Office Action, dated Jan. 5, 2015 in U.S. Appl. No. 11/942,687.
Interview Summary, dated Mar. 4, 2015 in U.S. Appl. No. 11/942,687.
PTAB Examiner's Answer, dated Feb. 25, 2016 in U.S. Appl. No. 11/942,687.
Final Office Action dated Oct. 22, 2012 in U.S. Appl. No. 11/944,027.
Notice of Allowance dated Jun. 5, 2013 in U.S. Appl. No. 11/944,027.
Office Action dated Oct. 14, 2014 in U.S. Appl. No. 14/043,165.
Final Office Action dated Apr. 1, 2015 in U.S. Appl. No. 14/043,165.
Office Action dated Oct. 2, 2015 in U.S. Appl. No. 14/043,165.
Interview Summary dated Dec. 21, 2015 in U.S. Appl. No. 14/043,165.
Final Office Action dated Feb. 17, 2016 in U.S. Appl. No. 14/043,165.
Notice of Allowance dated Oct. 15, 2012 in U.S. Appl. No. 12/622,404.

(56) References Cited

OTHER PUBLICATIONS

Office Action dated Mar. 17, 2015 in U.S. Appl. No. 13/768,765.
Interview Summary dated Jun. 11, 2015 in U.S. Appl. No. 13/768,765.
Notice of Allowance dated Aug. 28, 2015 in U.S. Appl. No. 13/768,765.
Notice of Allowability dated Nov. 20, 2015 in U.S. Appl. No. 13/768,765.
Notice of Allowability dated Jul. 28, 2016 in U.S. Appl. No. 13/768,765.
Office Action dated Mar. 4, 2013 in U.S. Appl. No. 12/891,543.
Interview Summary dated Apr. 5, 2013 in U.S. Appl. No. 12/891,543.
Notice of Allowance dated Nov. 14, 2013 in U.S. Appl. No. 12/891,543.
Office Action dated Sep. 11, 2014 in U.S. Appl. No. 14/179,328.
Notice of Allowance dated Jan. 14, 2015 in U.S. Appl. No. 14/179,328.
Office Action dated Aug. 13, 2015 in U.S. Appl. No. 14/687,853.
Notice of Allowance dated Feb. 25, 2016 in U.S. Appl. No. 14/687,853.
Supplemental Notice of Allowance dated Jun. 2, 2016 in U.S. Appl. No. 14/687,853.
Notice of Allowance dated Aug. 11, 2016 in U.S. Appl. No. 15/163,600.
Supplemental Notice of Allowance dated Sep. 14, 2016 in U.S. Appl. No. 15/163,600.
Office Action dated Jun. 27, 2014 in U.S. Appl. No. 13/572,397.
Final Office Action dated Jan. 13, 2015 in U.S. Appl. No. 13/572,397.
Notice of Allowance dated Mar. 19, 2015, 2015 in U.S. Appl. No. 13/572,397.
Office Action dated Aug. 6, 2014 in U.S. Appl. No. 13/572,547.
Notice of Allowance, dated Mar. 3, 2015 in U.S. Appl. No. 13/572,547.
Corrected Notice of Allowance, dated Apr. 10, 2015 in U.S. Appl. No. 13/572,547.
Corrected Notice of Allowance, dated May 21, 2015 in U.S. Appl. No. 13/572,547.
Office Action dated Jul. 30, 2014 in U.S. Appl. No. 13/572,552.
Interview Summary dated Sep. 3, 2014 in U.S. Appl. No. 13/572,552.
Final Office Action dated Jan. 28, 2015 in U.S. Appl. No. 13/572,552.
Interview Summary dated Apr. 23, 2015 in U.S. Appl. No. 13/572,552.
Notice of Allowance, dated May 8, 2015 in U.S. Appl. No. 13/572,552.
U.S. Appl. No. 14/540,830, Systems and Methods for Viewing Medical Images, filed Nov. 13, 2014.
U.S. Appl. No. 15/254,627, Systems and Methods for Interleaving Series of Medical Images, filed Sep. 1, 2016.
U.S. Appl. No. 14/095,123, Systems and Methods for Retrieval of Medical Data, filed Dec. 3, 2013.
U.S. Appl. No. 15/292,006, Systems and Methods for Viewing Medical 3D Imaging Volumes, filed Oct. 12, 2016.
U.S. Appl. No. 15/346,530, Systems and Methods for Matching, Naming, and Displaying Medical Images, filed Nov. 8, 2016.
U.S. Appl. No. 14/298,806, Smart Placement Rules, filed Jun. 6, 2013.
U.S. Appl. No. 11/942,687, Smart Forms, filed Nov. 19, 2007.
U.S. Appl. No. 14/043,165, Automated Document Filings, filed Oct. 1, 2013.
U.S. Appl. No. 15/292,014, System and Method of Providing Dynamic and Customizable Medical Examination for, filed Oct. 12, 2016.
U.S. Appl. No. 15/292,023, Selective Display of Medical Images, filed Oct. 12, 2016.
U.S. Appl. No. 14/792,210, Dynamic Montage Reconstruction, filed Jul. 6, 2015.
U.S. Appl. No. 15/188,872, Intelligent Management of Computerized Advanced Processing, filed Jun. 21, 2016.
U.S. Appl. No. 15/188,819, Intelligent Management of Computerized Advanced Processing, filed Jun. 21, 2016.
U.S. Appl. No. 15/140,346, Database Systems and Interactive User Interfaces for Dynamic Interaction With, and Sorting of, Digital Medical Image Data, filed Apr. 27, 2016.
U.S. Appl. No. 15/140,363, Database Systems and Interactive User Interfaces for Dynamic Interation With, and Comparison of, Digital Medical Image Data, filed Apr. 27, 2016.
U.S. Appl. No. 15/140,351, Database Systems and Interactive User Interface for Dynamic Interaction With, and Review of, Digital Medical Image Da, filed Apr. 27, 2016.
U.S. Appl. No. 15/140,348, Database Systems and Interactive User Interfaces for Dynamic Interation With, and Indications of, Digital Medical Image Data, filed Apr. 27, 2016.
Office Action dated Jan. 17, 2017, in U.S. Appl. No. 14/540,830.
Office Action dated Dec. 12, 2016, in U.S. Appl. No. 15/254,627.
Corrected Notice of Allowance dated Oct. 21, 2016 in U.S. Appl. No. 14/081,225.
Corrected Notice of Allowance dated Nov. 16, 2016 in U.S. Appl. No. 14/244,431.
Appeal Brief dated Jul. 15, 2016 in U.S. Appl. No. 14/043,165.
Examiner's Answer dated Nov. 14, 2016, in U.S. Appl. No. 14/043,165.
Office Action, dated Jan. 12, 2017 in U.S. Appl. No. 15/292,023.
Restriction Requirement, dated Jul. 28, 2015 in U.S. Appl. No. 14/139,068.
Office Action, dated Mar. 11, 2016 in U.S. Appl. No. 14/139,068.
Notice of Allowance, dated Sep. 21, 2016 in U.S. Appl. No. 14/139,068.
Sprawls, "Image Characteristics and Quality," Physical Principles of Medical Imaging, http://www.sprawls.org/resources pp. 1-14.
TeraRecon iNtuition pamphlet in 20 pages, retrieved on Nov. 8, 2013, available at http://int.terarecon.com/wp-content/uploads/2013/11/brochure_english2013.pdf.
TeraRecon iNtuition—Workflow. <www.terarecon.com/wordpress/our-solutions/intuition-workflow> Last accessed Nov. 8, 2013. 2 pages.
Interview Summary dated Mar. 24, 2017, in U.S. Appl. No. 14/540,830.
Notice of Allowance dated Mar. 30, 2017, in U.S. Appl. No. 14/095,123.

\* cited by examiner

FIG. 8

Procedures

Modality: CT with IV Contrast ▼        Search By: Name ▼

Select one or more Procedures:

| ---- Available Procedures ---- | ---- Selected Procedures ---- |
|---|---|
| ANGIOGRAPHY ABDOMEN W (52534) | ANGIOGRAPHY CHEST W (59502) |
| ANGIOGRAPHY CHEST W (59502) | |
| ANGIOGRAPHY HEAD W (59500) | |
| CERVICAL FACET INJECT BILAT (58418) | |
| CERVICAL SPINE W (54504) | |
| CHEST W (51407) | |
| CHEST W LMT (51506) | |
| CHEST W ABD WO-W (51412) | |
| CHEST W-ABD WO-W-PELV W (51404) | |
| CHEST W-AORTIC ANEURYSM (51411) | |

Details

Note: You must fill in any required warning and question(s) to proceed! ANGIOGRAPHY CHEST W

Warnings

- 910B — ☐ NO HISTORY OF LIFE THREATENING ALLERGIC REACTION (If YES, alternative study may be recommended)*
- 910A — ☐ NO RECENT SEVERE ASTHMA ATTACK (If YES, alternative study may be recommended)*

Questions

- 912A — Have you been here before?        *select one* ▼
- 912B — Do you have insurance?             *select one* ▼
- 912C — HIVES OR ALLERGIES? (specify reaction)
- 912D — INHALER? (specify type)
- 912E — OVER 65, DIABETIC or RENAL DISEASE? (BUN/CR with DATE<90 days)
- 912F — METFORMIN (Fortamet, Glucophage, Riomet, Diaformin, Diabex, Glumetza)?     *select one* ▼
- 914A — *PREGNANT?        *select one* ▼
- 914B — *WEIGHT?
- 912G — PRIOR RELATED IMAGING? (location/date)
- 912H — REMARKS:

Information

- 916A — For more information regarding this exam click here
- 916B — If on DIALYSIS, schedule appt within 24 hours of the next dialysis appt.
- 916C — Normal renal function is typically documented with serum BUN and CREATININE before

FIG. 9

Procedures

Modality: CT with IV Contrast          Search By: Name

Select one or more Procedures:

---- Available Procedures ----
ANGIOGRAPHY ABDOMEN W (52534)
ANGIOGRAPHY CHEST W (59502)
ANGIOGRAPHY HEAD W (59500)
CERVICAL FACET INJECT BILAT (58418)
CERVICAL SPINE W (54504)
CHEST W (51407)
CHEST W LMT (51506)
CHEST W ABD WO-W (
CHEST W-ABD WO-W-P
CHEST W-AORTIC ANEL ---- Selected Procedures ----
ANGIOGRAPHY CHEST W (59502)

— 1010

Microsoft Internet Explorer

⚠ A required warning has not been acknowledged.
Click on OK and checkmark the following warning to proceed:

NO HISTORY OF LIFE THREATENING ALLERGIC REACTION (If YES, alternative study may be recommended)

[ OK ]

Note: You must fill in a
Warnings
☐ NO HISTORY OF LI
  recommended)*
☐ NO RECENT SEVERE

Questions

| | |
|---|---|
| Have you been here before? | *select one* ▼ |
| Do you have insurance? | *select one* ▼ |
| HIVES OR ALLERGIES? (specify reaction) | |
| INHALER? (specify type) | |
| OVER 65, DIABETIC or RENAL DISEASE? (BUN/CR with DATE<90 days) | |
| METFORMIN (Fortamet, Glucophage, Riomet, Diaformin, Diabex, Glumetza)? | *select one* ▼ |
| *PREGNANT? | *select one* ▼ |
| *WEIGHT? | |
| PRIOR RELATED IMAGING? (location/date) | |
| REMARKS: | |

Information

- For more information regarding this exam click here
- If on DIALYSIS, schedule appt within 24 hours of the next dialysis appt.
- Normal renal function is typically documented with serum BUN and CREATININE before

FIG. 10

*DR SYSTEMS*
RIS•PACS PERFORMANCE SOLUTIONS

ADMINISTRATIVE DESK   Logout

Facility   BUMBLEBEE ▼           Apply Changes   1200

Maintenance
  Service Account
  Facility
  Assign to Facility
  Modality
  Suites
  Staff Type
  Staff Member
  Equipment
  Procedures
  Book Views
  Insurance
  Insurance Type
  Insurance Precert Req.
  Practice,Physician,Office
  Patients
  Patient Types
  Account Types
  Cancel Codes
  Reschedule Codes
  Relationship Type
  Security
  Configuration
  Language Conversion
  External Mapping
  HL7 Management
Reports
Help

Facility Administration

Search [          ] [Find]   View [Active ▼]   Order [Description ▼]

| Sel | ID | Description | Address | Phone | Status |
|-----|----|-------------|---------|-------|--------|
| ◉ | 13 | BUMBLEBEE | 2 BUMBLEBEE BUMBLEBEE WH 24156-0015 | 961-638-9515 | Active |
| ○ | 5 | EUREKA | 7 EUREKA EUREKA WH 24813 | 682-029-0229 | Active |
| ○ | 18 | GOOD SOUL | 10140 MESA RIM RD SAN DIEGO CA 92121 | 858 625 3344 | Active |

‹‹ ‹ 1 › ››   Refresh   Page 1 of 1   Rows per page: [20 ▼]

[Add] [Edit]   [Facility Setup]

[Schedule Notes]   [Exam Prep]   [Masks]

1210 (pointing to Facility)
1220 (pointing to Schedule Notes)

FIG. 12

EXAM SCHEDULING WITH CUSTOMER CONFIGURED NOTIFICATIONS

CROSS-REFERENCE TO RELATED APPLICATIONS

This application claims the benefit of U.S. Provisional Application No. 60/867,071, filed Nov. 22, 2006, which is hereby incorporated by reference in its entirety herein.

BACKGROUND OF THE INVENTION

Field of the Invention

This invention relates to scheduling of medical exams, and more particularly, to systems and methods for scheduling of medical exams with customer configured notifications, such as questions, warnings, and information.

Description of the Related Art

Medical exam scheduling typically comprises not only selecting a time and date for a patient to be examined, but also gathering of various information associated with the patient that may be useful by medical personnel responsible for preparing for and/or completing the exam, and may also be used in determining whether a particular exam requested for a patient is necessary and safe for the particular patient. Additionally, as part of a scheduling process various information may be requested from a patient from respective medical facilities and insurance companies, for example. Thus, questions and information provided to a patient, or a scheduler that is responsible for scheduling the patient's exam, may vary from patient to patient based on one or more of several factors, such as a requested exam modality, procedure, medical facility, insurance type, medical history, patient age or age category, various patient demographics, and/or any other related characteristics associated with the patient.

SUMMARY OF THE INVENTION

In one embodiment, a method of creating a data structure for associating exam parameters with respective notifications for presentation to a scheduler comprises receiving an indication of an exam parameter, receiving notification text associated with the exam parameter, receiving an indication of a type of notification associated with the notification text, the type of notification selected from the group comprising at least a first notification type that requires a response from a scheduler and a second notification type that does not require a response from the scheduler, and storing in a data structure indications of the exam parameter, the notification text, and the notification type, so that the notification text and notification type are associated with the exam parameter.

In one embodiment, a computerized method of scheduling a patient for a medical exam comprises receiving patient information comprising data identifying a specific patient, determining exam parameters indicating one or more of an exam type, an exam modality, and a medical facility, selecting one or more notifications for display to the scheduler, wherein the notifications are selected based on one or more of the exam parameters and at least one of the notifications comprises a hard question that requires a response from the scheduler before scheduling of the exam may be completed, and presenting the selected one or more notification to the scheduler.

In one embodiment, a system of scheduling a patient for a medical exam comprises a scheduling device configured to receive one or more exam parameters from a computing device operated by a scheduler, the exam parameters comprising data associated with a requested medical exam, a storage device storing information associating a first plurality of exam parameters with at least one hard question and a second plurality of exam parameters with at least one soft question, wherein the hard questions comprise questions that must be answered in order to proceed further with scheduling and the soft questions comprise questions that are not required to be answered prior to proceeding with scheduling, and a notification module configured to access the received exam parameters and to select one or more hard questions and one or more soft questions associated with respective exam parameters as indicated in the information stored in the storage device, wherein the exam scheduling module is further configured to present the selected hard questions and soft questions to the scheduler.

BRIEF DESCRIPTION OF THE DRAWINGS

FIG. 8 is one embodiment of a user interface configured to receive indications from the scheduler regarding a selected one or more procedures.

FIG. 9 is one embodiment of a user interface including warnings, soft questions, hard questions, and information notifications.

FIG. 10 illustrated the user interface of FIG. 9, wherein at least one of the hard questions or warnings did not receive an acceptable response from the scheduler.

FIG. 12 illustrates the administrative user interface of FIG. 11 with a facility administration window that may be accessed by an authorized administrator of the exam scheduling system.

DETAILED DESCRIPTION OF THE PREFERRED EMBODIMENT

Figure 1:
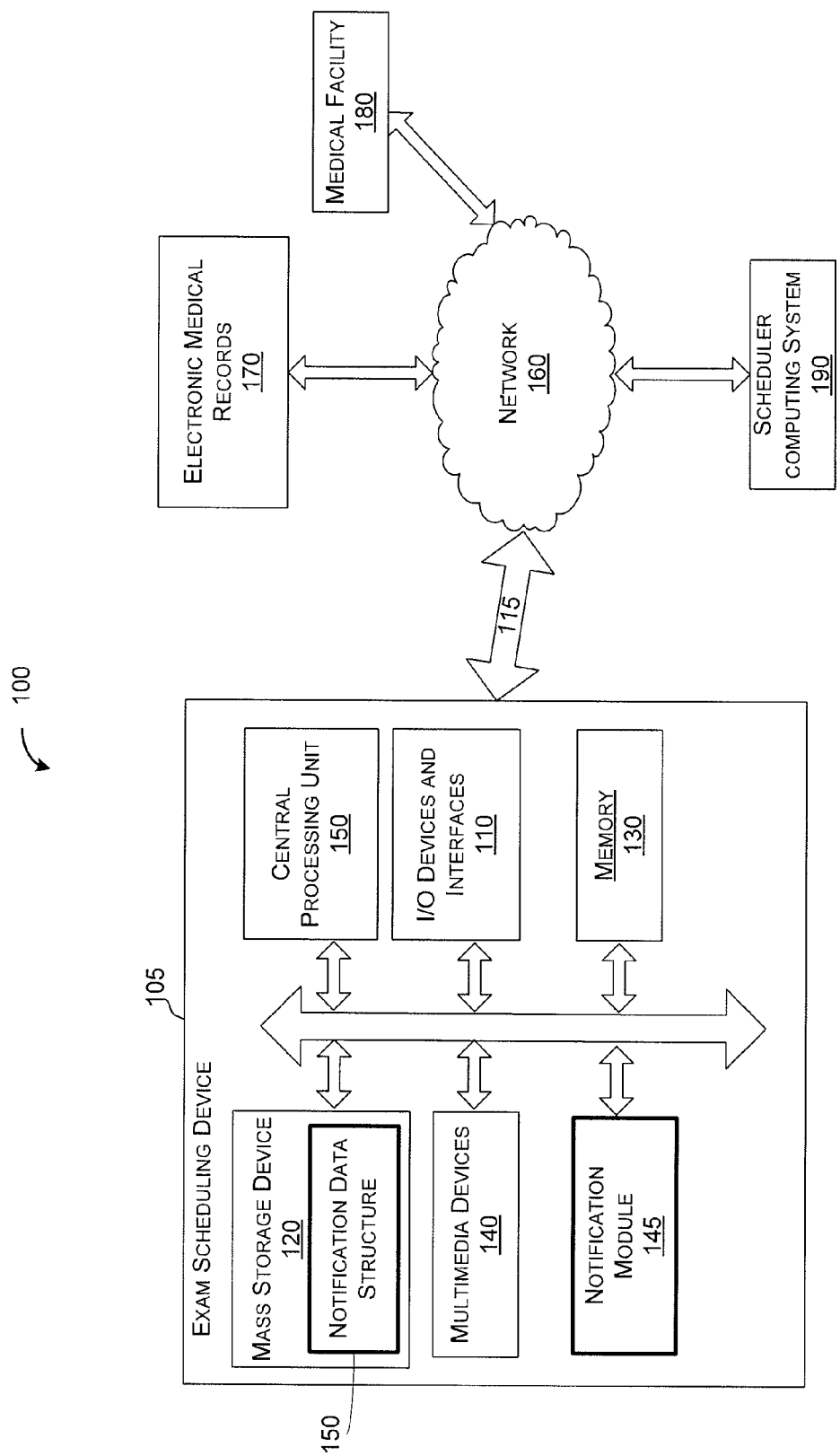
FIG. 1 is one embodiment of a block diagram of a computing system comprising an exam scheduling device in communication with a network and various networked devices.

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

The term "scheduler," as used herein describes one or more persons that interact with a computerized device in order to facilitate scheduling of an exam for a patient. Depending on the embodiment, the scheduler may be the patient for which the exam is to be scheduled, a relative of the patient, such as a parent or sibling of the patient, a clerical worker, such as a receptionist at a medical facility, a scheduling agent, such as a representative that handles exam scheduling for one or more medical facilities at a call center, for example, or any other person that is involved with scheduling an exam for a patient.

The term "exam parameters" describes characteristics or attributes of a patient, an exam, or anything related to the patient or exam. For example, exam parameters may include an exam modality, a procedure, a medical facility, an insurance type, a medical history, a patient age or age category, various patient demographics, a language, and/or any other related characteristics associated with the patient.

The term "notification" as used herein, refers to messages that are displayed to the scheduler, some of which require responses from the scheduler in order to proceed with scheduling of a requested exam. In one embodiment, notifications that may be presented to the scheduler include questions, warnings, and/or information. In one embodiment, questions request information from the scheduler, such as textual information that may be entered into a text entry field or information that may be selected from of one or more options provided to the scheduler, for example. In one embodiment, questions comprise "hard questions," which require an answer from the scheduler before continuing with scheduling of the exam, and "soft questions," which do not require an answer from the scheduler in order to continue with scheduling of the exam. In one embodiment, a "warning," as used herein, comprises information that is displayed to the scheduler that requires acknowledgment by the scheduler before allowing the exam to be scheduled. For example, a warning may require the scheduler to select a checkbox labeled "I acknowledge I have read this warning," or to otherwise acknowledge that the warning was read. In one embodiment, an "information" notification comprises information that is presented to the scheduler, which does not require any response or acknowledgement from the scheduler. For example, an information notification comprises information regarding medical procedures, medical facilities, medical equipment, or any other exam parameter.

FIG. 1 is a block diagram of a computing system 100 comprising an exam scheduling device 105 in communication with a network 160 and various networked devices. The computing system 100 may be used to implement certain systems and methods described herein. Depending on the embodiment, the functionality described below with reference to certain components and modules of the computing system 100 may be combined into fewer components and modules or further separated into additional components or modules. In one embodiment, the exam scheduling device 105 is operated by a scheduler, such as at a medical facility, at a scheduling facility, or from a computing device in communication with the scheduling device 105 via one or more networks. In one embodiment, certain scheduling operations of the exam scheduling device 105 are indicated by a scheduler computing system 190, which is controlled by a scheduler remote from the exam scheduling device.

The exemplary exam scheduling device 105 comprises a memory 130, such as random access memory (RAM) for temporary storage of information and a read only memory (ROM) for permanent storage of information, and a mass storage device 120, such as a hard drive, diskette, or optical media storage device. The mass storage device 120 may comprise one or more hard disk drive, optical drive, networked drive, or some combination of various digital storage systems. The exam scheduling device 105 also comprises a central processing unit (CPU) 150 for computation. Typically, the modules of the exam scheduling device 105 are in data communication via one or more standards-based bus system. In different embodiments, the standards based bus system could be Peripheral Component Interconnect (PCI), Microchannel, SCSI, Industrial Standard Architecture (ISA) and Extended ISA (EISA) architectures, for example.

The exam scheduling device 105 is generally controlled and coordinated by operating system software, such as the Windows 95, 98, NT, 2000, XP, Vista, or other compatible operating systems. In Macintosh systems, the operating system may be any available operating system, such as Mac OS X. In other embodiments, the exam scheduling device 105 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary exam scheduling device 105 includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. In one embodiment, a GUI includes one or more display panes in which medical images may be displayed. The exam scheduling device 105 may also include one or more multimedia devices 140, such as speakers, video cards, graphics accelerators, and microphones, for example.

In the embodiment of FIG. 1, the I/O devices and interfaces 110 provide a communication interface to various external devices. For example, the exam scheduling device 105 is in data communication with a network 160, such as a LAN, WAN, or the Internet, for example, via a wired or wireless communication link 115. In the exemplary embodiment of FIG. 1, the network 160 is in data communication with an electronic medical record (EMR) system 170, a medical facility 180, and a scheduler computing system 190. In addition to the devices that are illustrated in FIG. 1, the network 160 may facilitate communications with other computing, imaging, storage, and/or other electronic devices.

The exemplary EMR system 190 comprises hardware and/or software modules configured to store, manipulate and distribute patient data and imagery to one or more medical facilities and/or personnel. In one embodiment, the EMR system 190 comprises a radiology information system (RIS) used by a radiology department of a medical facility to store, manipulate, and distribute patient radiological data and imagery. The EMR system 190 may comprise patient information, such as patient biographical and medical history information, as well as scheduling information, such as scheduled exams for patients. In one embodiment, the EMR system 190 provides medical data from multiple sources to the exam scheduling device 105 via the network 160 and the communication link 115.

In the embodiment of FIG. 1, the scheduler computing system 190 is a computing device operated by a scheduler. For example, the computing system 190 may comprise a desktop PC or Macintosh computing system, laptop, notebook, mobile device, cellphone, kiosk, or any other electronic device that can suitably communicate with the exam scheduling device 105.

The exemplary exam scheduling device 105 comprises a notification module 145 configured to determine notifications for display to a scheduler in the process of scheduling an exam. As described in further detail below, notifications presented to the scheduler may be selected based on the exam parameters selected by a scheduler, for example. Thus, only those notifications that are relevant to the exam parameters associated with a particular patient's exam are presented to the scheduler, and the scheduler is required to respond to only those notifications that a scheduling administrator has determined require a response.

Figure 2:
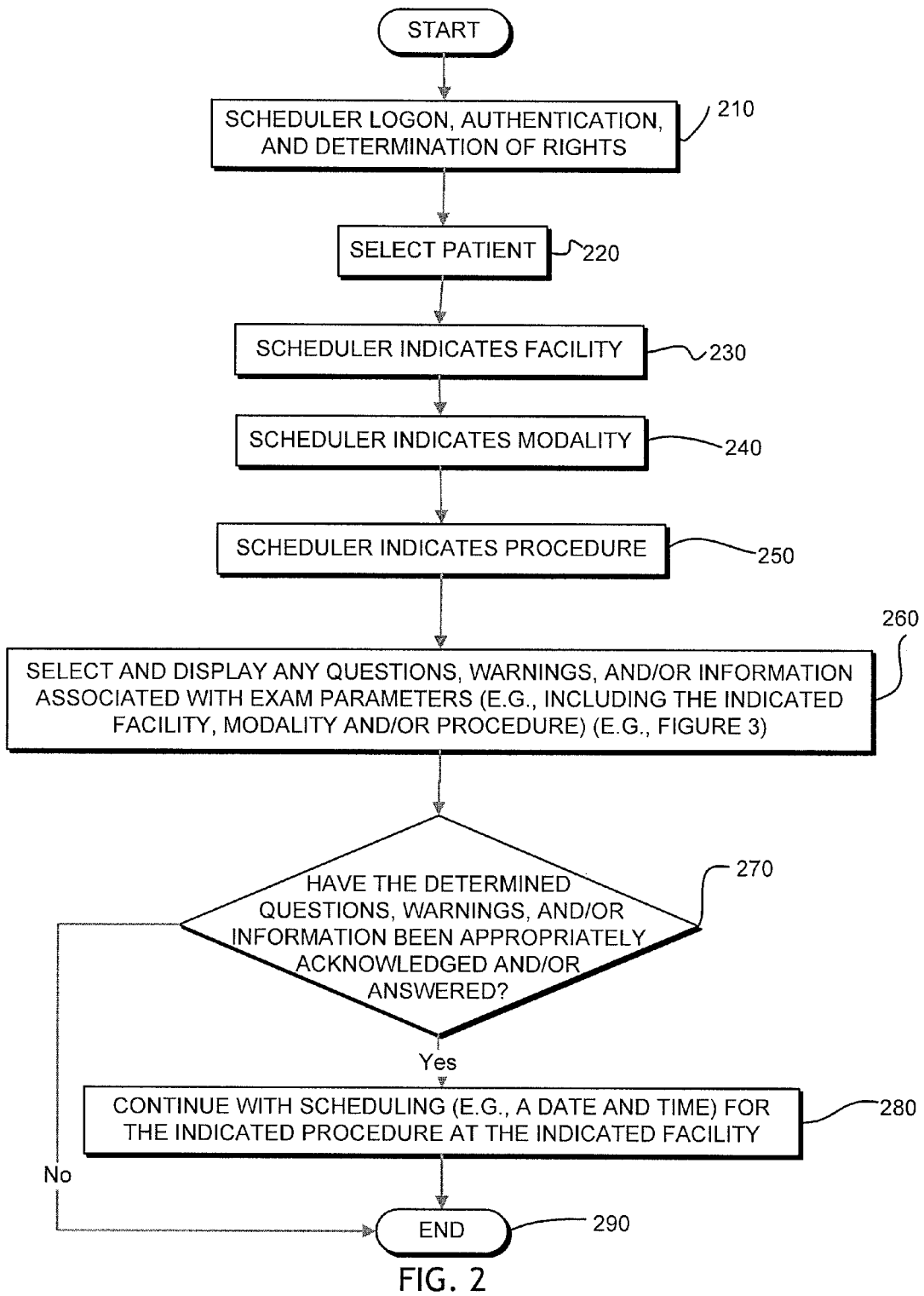
FIG. 2 is one embodiment of a flowchart illustrating one embodiment of a method of providing notifications to a scheduler as part of a scheduling process.

FIG. 2 is a flowchart illustrating one embodiment of a method of providing notifications to a scheduler as part of a scheduling process. As described further below, depending on the exam parameters, the exam scheduling device 105 presents the scheduler with one or more notifications, which may comprise one or more hard questions, soft questions, warnings, and/or information. In other embodiments, the notifications comprise fewer types, such as only hard questions and software questions. Depending on the embodiment, the method of FIG. 2 may include fewer or additional blocks and the method may be performed in a different order than as illustrated.

For ease of description, the method of FIG. 2 will be described in conjunction with FIGS. 4-10, which illustrate exemplary user interfaces that may be presented to the scheduler. In one embodiment, the user interfaces of FIGS. 4-10 are generated by the exam scheduling device 105 and transmitted to the scheduler computing system 190 via the network 160. In one embodiment, the user interfaces are viewable in an Internet browser, while in other embodiments, the user interfaces are presented to the scheduler via standalone scheduling software that is running on one or more of the exam scheduling device 105 and/or scheduler computing system 190.

Beginning in block 210, a scheduler directly accesses an input device coupled to the exam scheduling device 105 or establishes a communication link between the scheduler computing device 190 in order to exchange data with the notification module 145. In one embodiment, the scheduler logs onto the exam scheduling device 190, is authenticated, and allow the exam scheduling device 105 to determine rights of the scheduler to schedule exams. In one embodiment, the process of block 210 is performed in response to the scheduler providing login information to the exam scheduling device 105. For example, the scheduler may enter a username and password in order to be authenticated by the exam scheduling device 105. In one embodiment, a scheduling rights data structure is maintained by the exam scheduling device 105 in order to allow determination of the scheduler's rights to schedule an exam for a particular patient. For example, a scheduler that is also the patient may have only rights to schedule an exam for him/herself. However, a scheduler that is a receptionist at a medical facility may have rights to schedule an exam for any patient. In one embodiment, the exam parameters include an experience level of the scheduler, such as an indication of whether the scheduler is a patient or administrative personnel that regularly performs scheduling operations for patients.

Figure 4:
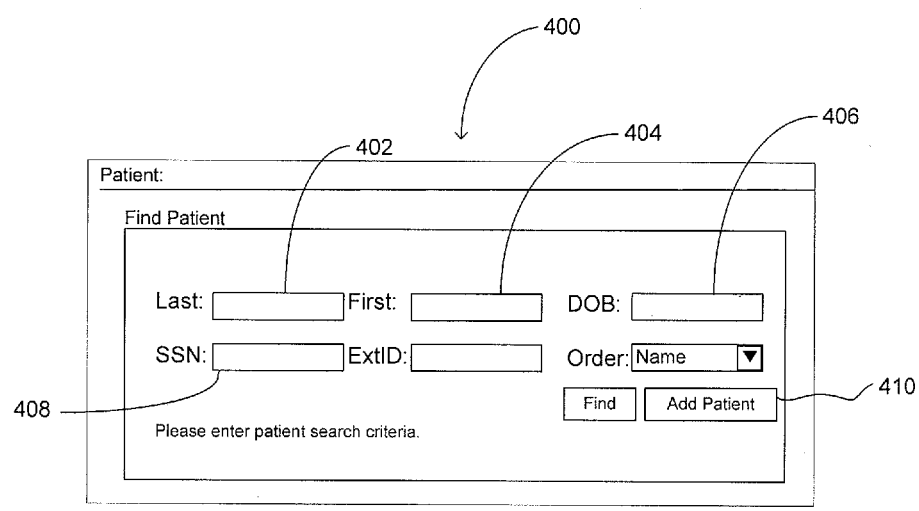
FIG. 4 illustrates one embodiment of a user interface that allows a scheduler to select a patient for scheduling an exam.

Moving to block 220, a patient for which an exam is to be scheduled is selected, such as from a plurality of patient in an EMR system. In one embodiment, the scheduler provides a patient identification number, such as a medical records number or Social Security number, in order to identify the patient. In other embodiments, other patient information, such as last name, first name, and/or contact information of the patient, may be provided in order to identify the patient. FIG. 4 illustrates one embodiment of a user interface 400 for selecting a patient. The user interface 400 comprises a last name field 402, a first name field 404, a date of birth field 406, and a Social Security number field 408 that are each configured to receive information from the scheduler that may be used to locate a particular patient. Depending on the embodiment, a patient may be located by providing patient information in as few as one of the fields 402, 404, 406, 408. For example, in one embodiment a patient may be located by entering only a last name of the patient in field 402 or a Social Security number of the patient in field 408. In the embodiment of FIG. 4, the user interface 400 comprises an add patient button 410 that may be selected in order to add a new patient to the medical records software.

Moving to block 230, the scheduler indicates a facility at which the desired exam should be scheduled. In one embodiment, the scheduler may indicate multiple facilities, such as any available facilities within a provided geographic region. In another embodiment, a list of available facilities is presented to the scheduler, from which the scheduler can pick one or more facilities for scheduling of the exam.

Figure 5:
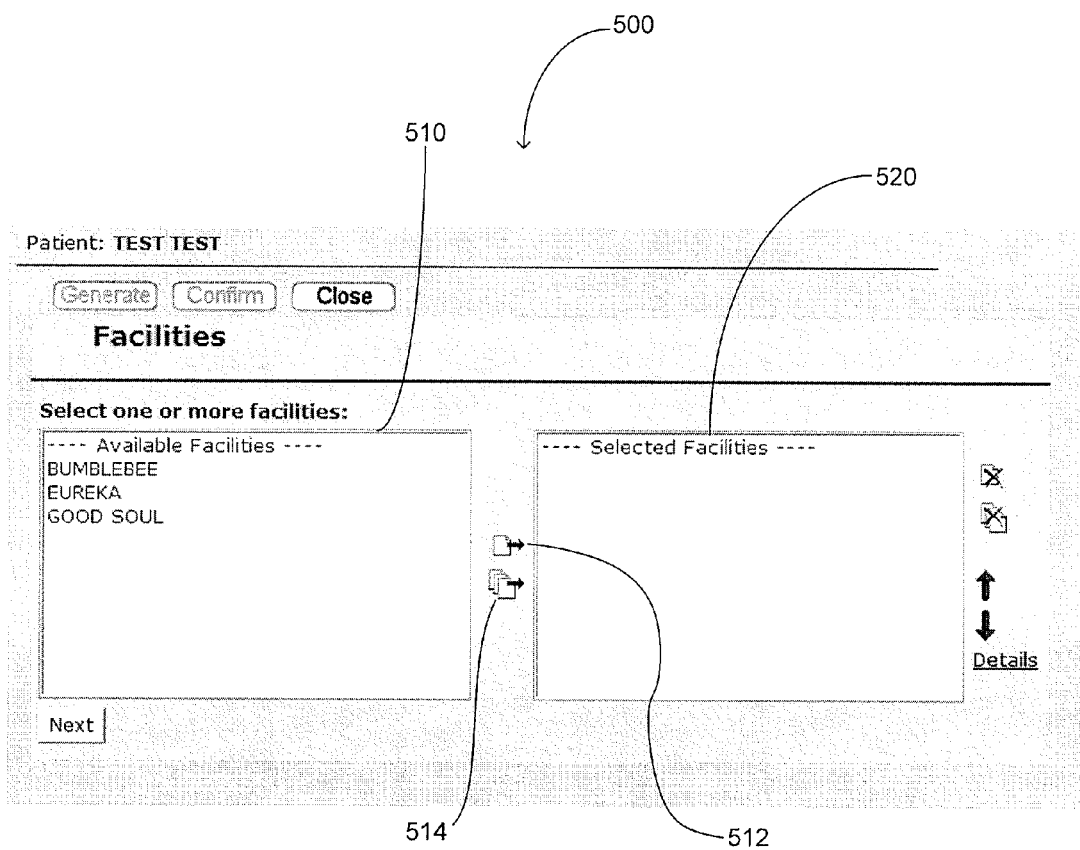
FIG. 5 illustrates one embodiment of a user interface that facilitates selection of a medical facility by the scheduler.

FIG. 5 is an exemplary user interface 500 that may be presented to the scheduler in order to facilitate selection of a medical facility. In the embodiment of FIG. 5, the user interface 500 comprises a facilities list pane 510 and a selected facilities pane 520. In the facilities list pane 510, one or more facilities are listed for selection by the scheduler. In one embodiment, the facilities listed in facilities list pane 510 are those that have been preselected by the scheduler or patient as preferred facilities. In one embodiment, the facilities listed in the facilities list pane 510 are those facilities that are partners with the patient's insurance provider. In other embodiments, the facilities listed in the facilities list pane 510 may be selected from a plurality of available facilities based on one or more characteristics of the patient and/or the particular facility. In the embodiment of FIG. 5, the scheduler selects a facility by clicking on the desired facility indicator and then selecting the selection button 512. For example, if the scheduler clicks on the Eureka facility listed in facilities list pane 510 and then clicks the selection button 512, the Eureka facility would be moved to the selected facilities pane 520, indicating that the scheduler is attempting to schedule an exam at the Eureka facility. The user interface 500 also comprises a select all button 514 that selects all of the listed facilities in the facilities list pane 510. Those of skill in the art will recognize that there are various other user interfaces, forms, and form controls, that may be used in order to receive indications from the scheduler of one or more facilities. FIG. 5 illustrates only one exemplary user interface; however, the systems and methods described herein are operational with any suitable variations thereof.

Figure 6:
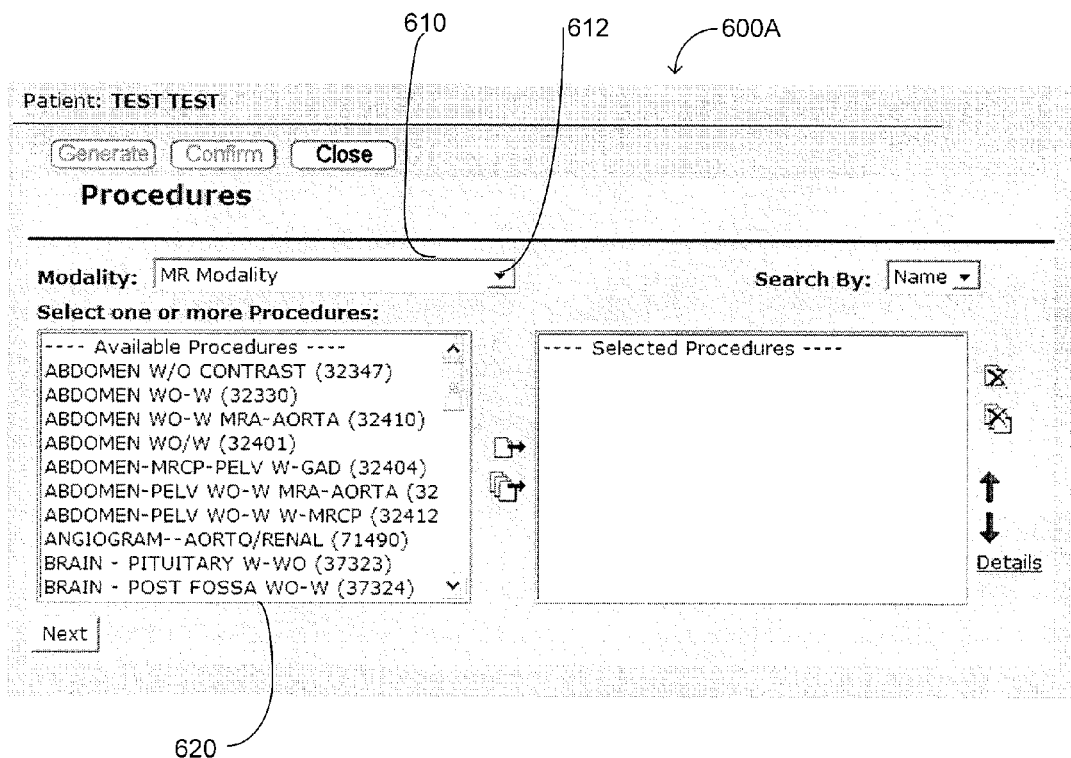
FIGS. 6 and 7 illustrate one embodiment of a user interface configured to receive input from the scheduler in order to select a modality.
Figure 7:
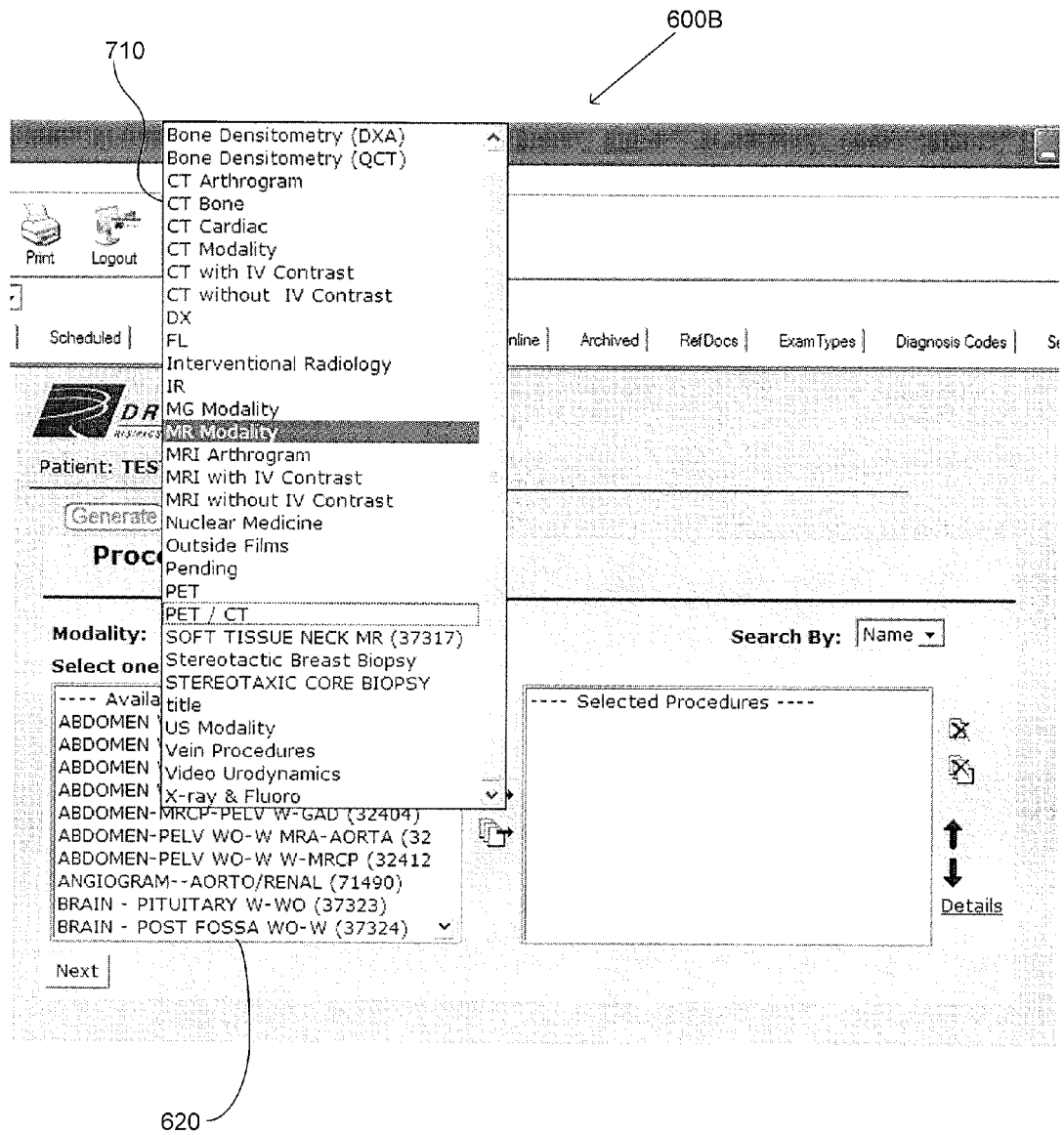

Moving to block 240, the scheduler indicates a modality of exam for the selected patient. "Modality," as used herein, describes a medical imaging device, such that a patient that undergoes an MRI is said to have been scanned with the MRI modality. Thus, modalities may include CTs of many varieties (e.g., CT Arthrogram, CT bone, CG cardiac, etc.), MRIs of many varieties, PET scans, ultrasounds, x-rays, and scans from any other available imaging device. FIGS. 6 and 7 illustrate a user interface 600 configured to receive input from the scheduler in order to select a modality. In the embodiment of FIG. 6, a modality selection field 610 indicates a currently selected modality. By selecting the modality selection button 612, a listing 710 (FIG. 7) of available modalities is provided. The listing 710 allows the scheduler to view available modalities and to select one or more of the modalities, such as by clicking on an indicator associated with the desired modality. Depending on the embodiment, other form controls may be used to allow the scheduler to select one or more desired modalities. In embodiment of FIGS. 6 and 7, selection of a modality initiates population of the procedures pane 620 with the available procedures for the selected modality.

Figure 8:
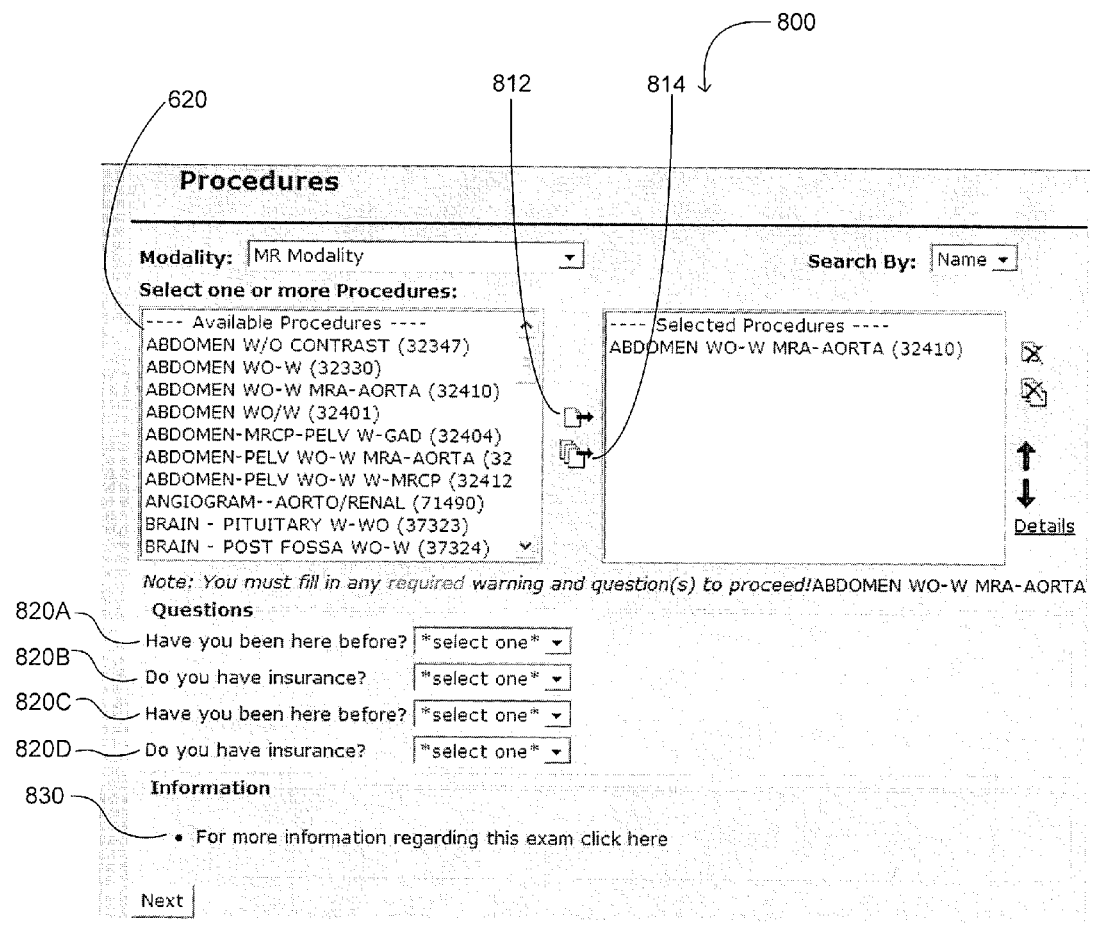

Next, in block 250, the scheduler indicates one or more procedures for which an exam is to be scheduled. As noted above, in one embodiment the procedures available for selection by the scheduler are determined by one or more of the exam parameters, such as the facility and/or modality selected by the scheduler. FIG. 8 is one embodiment of a user interface configured to receive indications from the scheduler regarding a selected one or more procedures. The exemplary user interface 800 comprises the procedures pane 620 that lists those procedures available for the selected modality (e.g., MR modality in the embodiment of FIG. 8). The scheduler may select a single procedure by clicking on the indication of the desired procedure in the procedures pane 620 and then selecting the selection button 812. Similarly, the scheduler may select all of the procedures indicated in the procedures pane 620 by clicking the select all button 814. The exemplary user interface 800 illustrates selection of one procedure, specifically, "ABDOMEN WO-W MR-AORTA (32410)". In other embodiments, various other forms and form controls may be used to select procedures. In one embodiment, for example, the scheduler may select a procedure (as well as the modality and facility) by speaking commands associated with the procedure into a microphone. In this embodiment, the exam scheduling device 105 may comprise voice-recognition logic that recognizes the commands spoken by the scheduler and performs actions in response to those commands.

Figure 3:
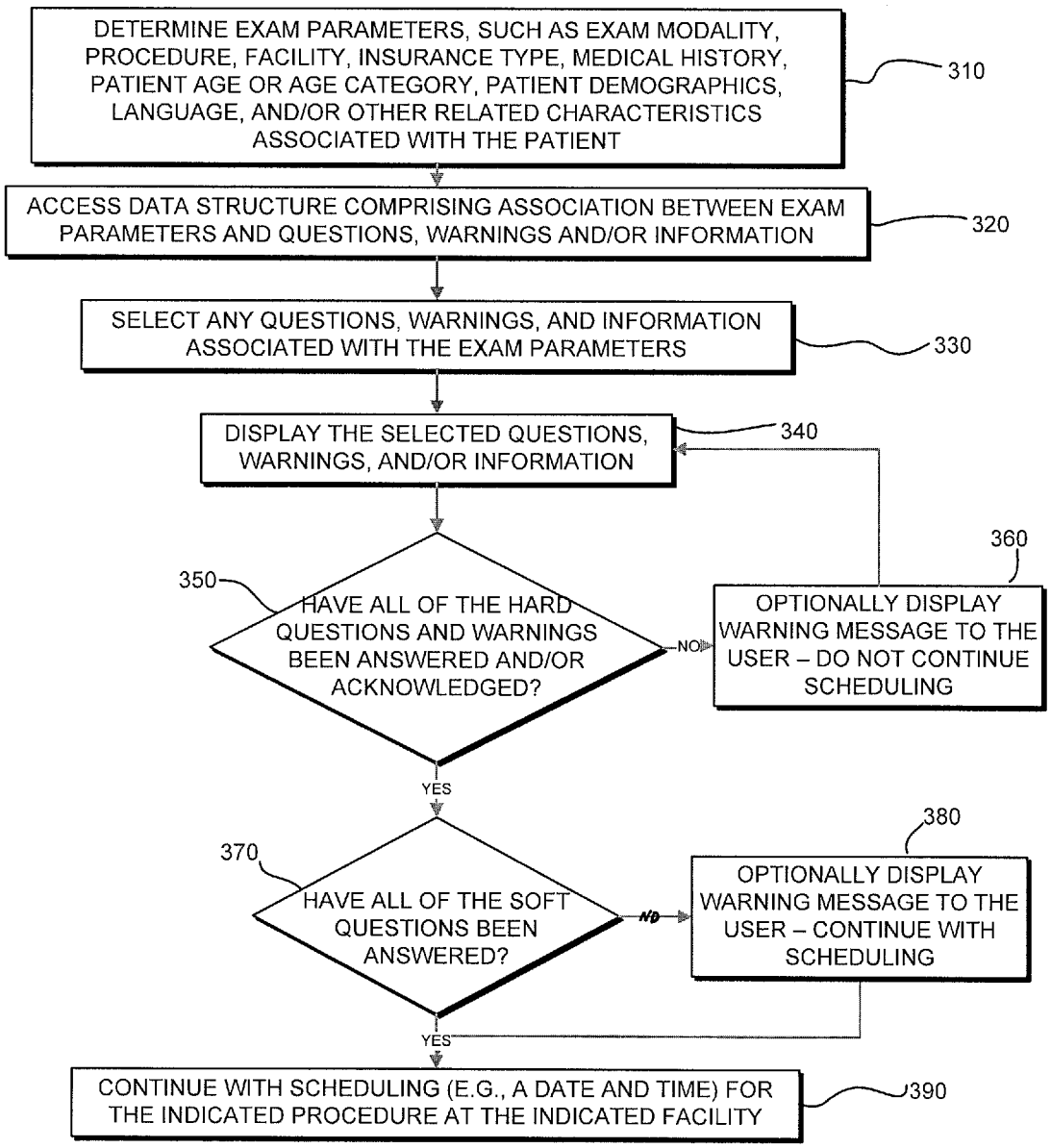
FIG. 3 is one embodiment of a flowchart illustrating a method of determining one or more notifications to be displayed to a scheduler, such as based on one or more exam parameters.

Moving to block 260, notifications associated with the exam parameters are selected and displayed to the scheduler. For example, notifications that are associated with the indicated facility, modality, procedure, and/or other exam parameters, are presented to the scheduler via a user interface. For example, in the user interface 800, four questions 820A, 820B, 820C, 820D and one information notification 830 are presented to the scheduler via the user interface 800. In one embodiment, the data structure 150 (FIG. 1) is accessed in order to determine the appropriate notifications for display to the scheduler, as well as the acknowledgments and/or other responses that might be required for certain notifications in order for the scheduler to complete scheduling of the exam. FIG. 3, described in detail below, illustrates an exemplary method of determining which notifications to display to the scheduler.

In block 270, the exam scheduling device determines if the notifications have been responded to in accordance with the requirements indicated in the data structure 150. For example, the notifications may comprise one or more hard questions that require answering by the scheduler. In this embodiment, if the scheduler has not satisfactorily answered each of the hard questions, the method continues to block 290, failing to complete scheduling of the exam. Similarly, if warnings that require acknowledgment by the scheduler are not acknowledged, the method continues to block 290. However, if the notifications comprise only soft questions and/or information, which do not require acknowledgment or response by the scheduler, the method continues to block 280 regardless of whether the scheduler has provided responses to the soft questions and/or information notifications.

In block 280, the scheduler is allowed to proceed with scheduling the exam for the patient, such as by selecting a particular date and time for the desired exam.

FIG. 3 is one embodiment of a flowchart illustrating a method of determining one or more notifications to be displayed to a scheduler, such as based on one or more exam parameters. Depending on the embodiment, the method of FIG. 3 may comprise fewer or additional blocks and blocks may be performed in different order than as illustrated in FIG. 3.

Beginning in block 310, one or more exam parameters are determined, such as by the exam scheduling device 105 in response to data provided by the scheduler and/or receiver from a medical records data store, for example. Thus, certain of the exam parameters may be received directly from the scheduler, such as is described above with respect to blocks 230, 240, 250 of FIG. 2, for example. Other exam parameters may be retrieved from one or more data structures comprising information regarding the patient, the requested exam, or other related information. For example, in one embodiment the exam scheduling device 105 accesses the EMR system 170 in order to access information associated with the patient, such as medical history, age, gender, language, etc., that may be included in the exam parameters used in determining notifications for display to the scheduler.

Moving to block 320, a data structure, such as the data structure 150 (FIG. 1), is accessed in order to identify notifications associated with the determined exam parameters. For example, the facility, modality, procedure, and/or other exam parameters may each be associated with one or more notifications, such as hard questions, soft questions, warnings, and/or information. Table 1, below, illustrates an exemplary data structure that may be used to store information regarding associations between exam parameters, notifications, and acceptable responses, if any.

TABLE 1

| Parameter | Parameter value | Notification text | Notification type | Acceptable response |
|---|---|---|---|---|
| Facility | Eureka | "Have you been to our facility before?" | Soft question | None required |
| Modality | CT with IV contrast | "Patient understands that fasting for at least 12 hours prior to the exam is required." | Warning | Yes |
| Procedure | Angiography Chest | "No history of life-threatening allergic reaction." | Warning | Yes |
| Procedure | Angiography Neck | "Weight?" | Hard | 15-90 |

TABLE 1-continued

| Parameter | Parameter value | Notification text | Notification type | Acceptable response |
|---|---|---|---|---|
| Age | <18 | "Has guardian authorization been provided to the scheduler" | Hard | Yes |

As illustrated in table 1, any parameter may be linked to notification text and a corresponding acceptable response. In the exemplary data structure of Table 1, the soft questions require no response, while the warnings and hard questions require a specific responses from the scheduler before the exam scheduling device 105 allows completion of the exam scheduling.

Moving to block 330, the exam scheduling device 105 selects any notifications that are associated with the determined exam parameters. For example, if one of the exam parameters is a modality of "CT with IV contrast", the exemplary data structure of table 1 indicates that a warning notification requiring a "yes" response should be provided to the scheduler.

Next, in block 340, any selected notifications are presented to the scheduler, such as via a user interface. FIG. 9 is one embodiment of a user interface 900 including warnings 910A and 910B, soft questions 912A-912H, hard questions 914A and 914B, and information notifications 916A, 916B, and 916C. In an advantageous embodiment, the various notifications 910, 912, 914, 916 are selected for presentation to the scheduler based on associations of one or more exam parameters with the particular notifications in the notification data structure 150. In one embodiment, the respective responses associated with the displayed notifications must be received by the exam scheduling device 105 before the exam scheduling device 105 allows completion of the exam scheduling. For example, if the warning of Table 1 associated with the "CT with IV contrast" is not responded to by the scheduler (e.g., such as by checking an acknowledgement box in the user interface 900) or if the scheduler responds with a "no" response, the method continues to block 360 and scheduling of the exam is halted.

In one embodiment, if the appropriate response for a notification is not provided by the scheduler, in block 360 an indication of the improper response is provided to the scheduler and the scheduler is given another opportunity to respond to the notification. For example, FIG. 10 illustrates the user interface of FIG. 9, including various notifications, wherein at least one of the hard questions or warnings did not receive an acceptable response from the scheduler. In the embodiment of FIG. 10, a warning messagebox 1010 is displayed to advise the scheduler that required information has not been provided. In one embodiment, a separate messagebox 1010 is displayed for each notification that did not receive an acceptable response from the scheduler, while in other embodiments, a single messagebox 1010 may indicate missing and/or unacceptable information associated with multiple notifications.

Moving to block 350, the exam scheduling device 105 determines if all of the notifications that require responses from the scheduler, if any, have received acceptable responses from the scheduler. As noted above, certain notifications do not require responses from the scheduler, while others may require a response of any type, and still others require a specific response from the scheduler in order to continue with scheduling of the exam. In block 350, the exam scheduling device 105 determines if acceptable responses have been provided for those notifications requiring a response, such as hard questions and warnings. If one or more of the hard questions and/or warnings have not received an acceptable response from the scheduler, the method continues to block 360 and exam scheduling cannot be completed. Alternatively, if any required responses to notifications are provided by the scheduler, the method continues to block 370.

In block 370, the method optionally determines whether all soft questions have been answered by the scheduler. In response to determining that not all soft questions have been answered by the scheduler, the method continues to block 380 where the scheduler is optionally provided with a warning message indicating that certain soft questions have not received responses. No matter if the soft questions have all been answered or if some have not been answered, the method moves to block 390 (which is equivalent to block 280 in FIG. 2) where further scheduling of the exam is facilitated by the exam scheduling device 105.

Figure 11:
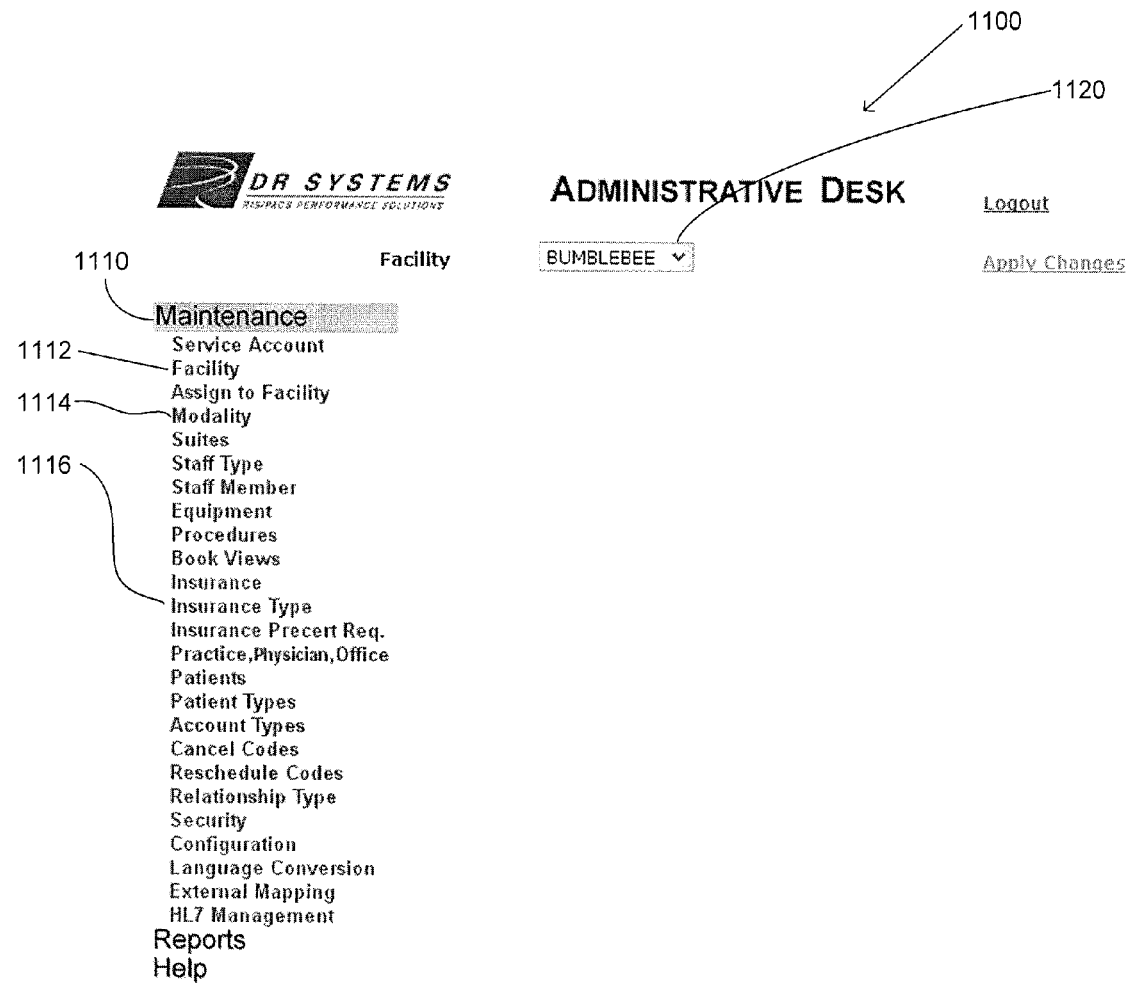
FIG. 11 is one embodiment of an administrative user interface that may be accessed by an authorized administrator of the exam scheduling device, for example, in order to add and/or edit notifications.

FIG. 11 is one embodiment of an administrative user interface 1100 that may be accessed by an authorized administrator of the exam scheduling device 105, for example, in order to add and/or edit notification rules, where a notification rule comprises an association between one or more exam parameters, a notification, and optionally a required response format and/or acceptable response(s). The user interface 1100 comprises a maintenance menu 1110 listing a plurality of menu items associated with notifications and other aspects of the notification module 145 that may be modified. For example, notification rules associated with a facility may be added and/or modified by selecting the facility option 1112, notification rules associated with an exam modality may be added and/or modified by selecting the modality option 1114, notification rules associated with an insurance type may be added and/or modified by selecting the insurance type option 1116, and notification rules associated with other exam parameters may be modified by selecting the option associated with the desired exam parameters in menu 1110. The exemplary user interface 1100 illustrates selection of the facility option 1112 by the administrator, and a selection tool 1120 that allows the administrator to select a specific facility for establishing and/or modifying notification rules. In this embodiment, the selection tool 1120 comprises a drop-down box that is pre-populated with the available facilities. In other embodiments, any other selection tools may be used to allow the administrator to select an exam parameter for adding and/or modifying.

FIG. 12 illustrates the user interface 1100 with a facility administration window 1200 that may be accessed by an authorized administrator of the exam scheduling system. In this embodiment, the facility administration window 1200 is provided in response to selecting the facility option 1112 (FIG. 11). If other exam parameters are selected from the menu 1110 (FIG. 11), the user interface 1100 may include a window similar to the facility administration window 1200 associated with the selected exam parameter. In the embodiment of FIG. 12, three facilities are listed for selection by the administrator. In the exemplary facility administration window 1200, the "Bumblebee" facility has been selected by the administrator by selecting the radio button selector 1210. With the desired facility (or other exam parameter) selected, modification and/or addition of notification rules begins by selecting the schedule notes button 1220.

Figure 13:
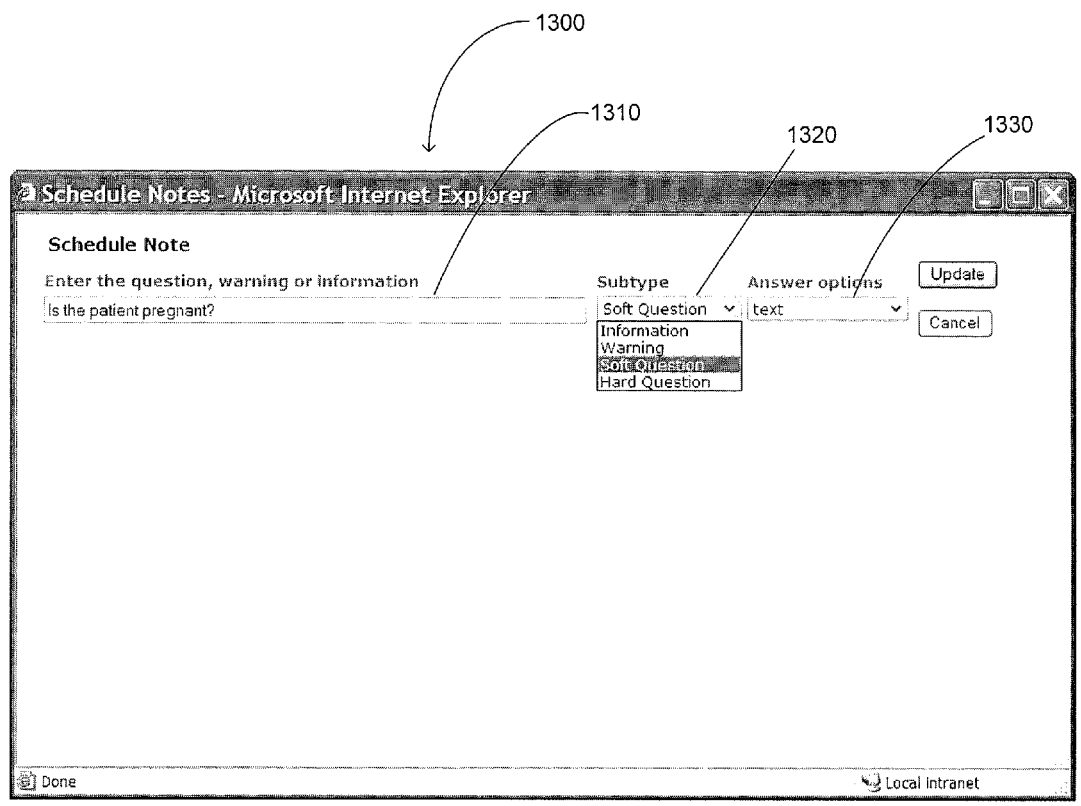
FIG. 13 illustrates a notification window that allows an administrator to add new notifications that are associated with a selected exam parameter.

FIG. 13 illustrates a notification window 1300 that allows an administrator to add new notification rules that are associated with a selected exam parameter. For example, if a facility is selected (e.g., FIG. 12), the notification window 1300 is used to establish notifications that are displayed to a scheduler in response to the scheduler selecting the particular facility. The notification window 1300 includes a notification text field 1310, a notification type field 1320, and a response type field 1330. The exemplary notification text field 1310 receives the notification text from an input device controlled by the administrator. in the exemplary embodiment of FIG. 13, the notification text is "Is the patient pregnant?" In other embodiments, the notification text comprises any other text information to be displayed to the scheduler, such as the text associated with a hard question, soft question, warning, and/or information notification. In one embodiment, the notification text entered into notification text field 1310 comprises standard ASCII characters, while in other embodiments the notification text comprises formatted text, such as HTML formatted text, or any other format. In one embodiment, notifications may include images, such as JPG or GIF images, for example.

The exemplary notification window 1300 also comprises a notification type field 1320 that defines a type of notification being created. In the embodiment of FIG. 13, the types comprise hard questions, soft questions, warnings, and information notifications. In other embodiments, fewer or additional notification types may be included in the notification type field 1320. For example, in one embodiment the notification types may include "response required", "acknowledgment required", and "no response or acknowledgement required."

Figure 14:
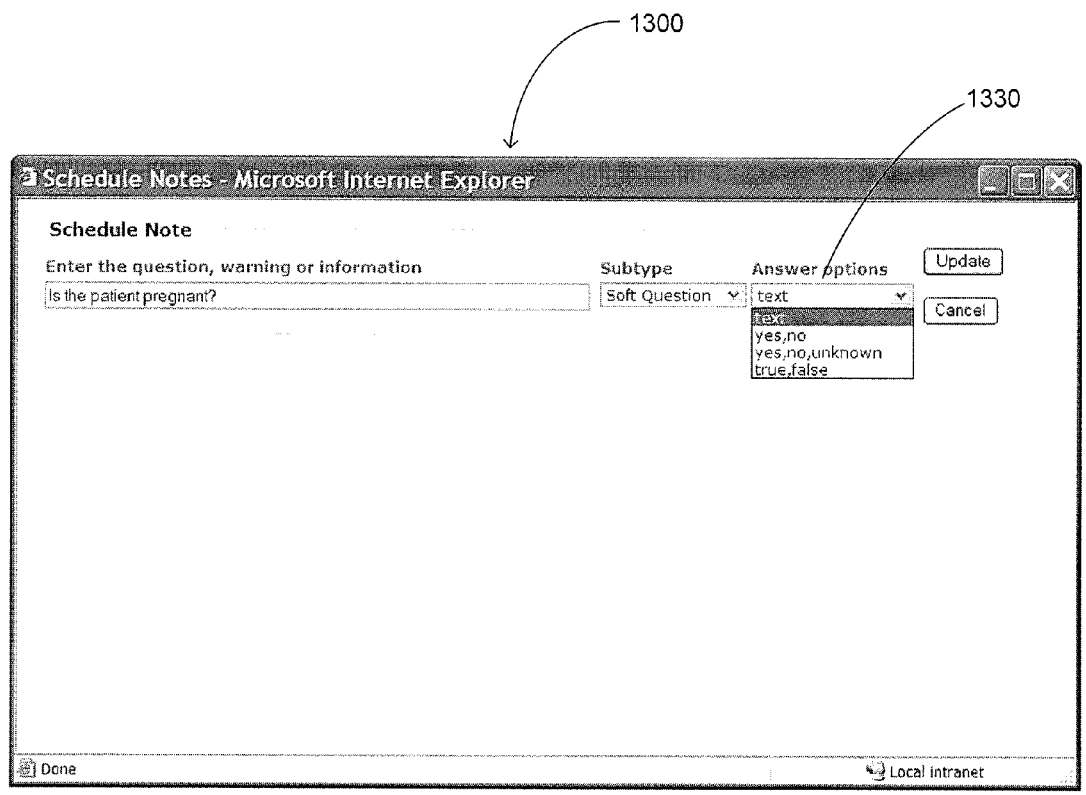
FIG. 14 illustrates the notification window of FIG. 13 with the answer options field expanded to show additional response options.

The answer options field 1330 of FIG. 13 comprises limitations on the types of responses available to the specific notification text entered into notification text field 1310. In the embodiment of FIG. 13, the notification text "Is the patient pregnant?" may be responded to with any textual characters, as indicated in the answer options field 1330. FIG. 14 illustrates the notification window 1300 with the answer options field 1330 expanded to show additional response options. In particular, the answer options field 1330 in FIG. 14 allows the administrator to limit the answer options available to a scheduler in response to the indicated notification to one or more of "text", "yes, no", "yes, no, unknown" and/or "true, false" responses. Depending on the embodiment, other answer options may be provided for selection and/or the administrator may be allowed to establish a unique rule for an acceptable answer, such as a regular expression that defines an acceptable answer.

In one embodiment, the notification window 1300 further comprises an acceptable responses field (not shown) in which the administrator indicates one or more responses to a notification that allow the scheduler to continue scheduling the examination. For example, because a pregnant patient may not be able to safely undergo certain modalities, an administrator may indicate that the only acceptable response to a notification asking "is the patient pregnant?" is "no". Thus, if the scheduler responds to such a notification with anything other than "no" the response is deemed unacceptable and the scheduler is not allowed to continue with scheduling of the exam. In other embodiments, if a response to a particular notification does not match an associated acceptable response, the scheduler may be allowed to continue scheduling of the exam, and a notice of the non-acceptable response is provided to the administrator or other personnel.

Figure 15:
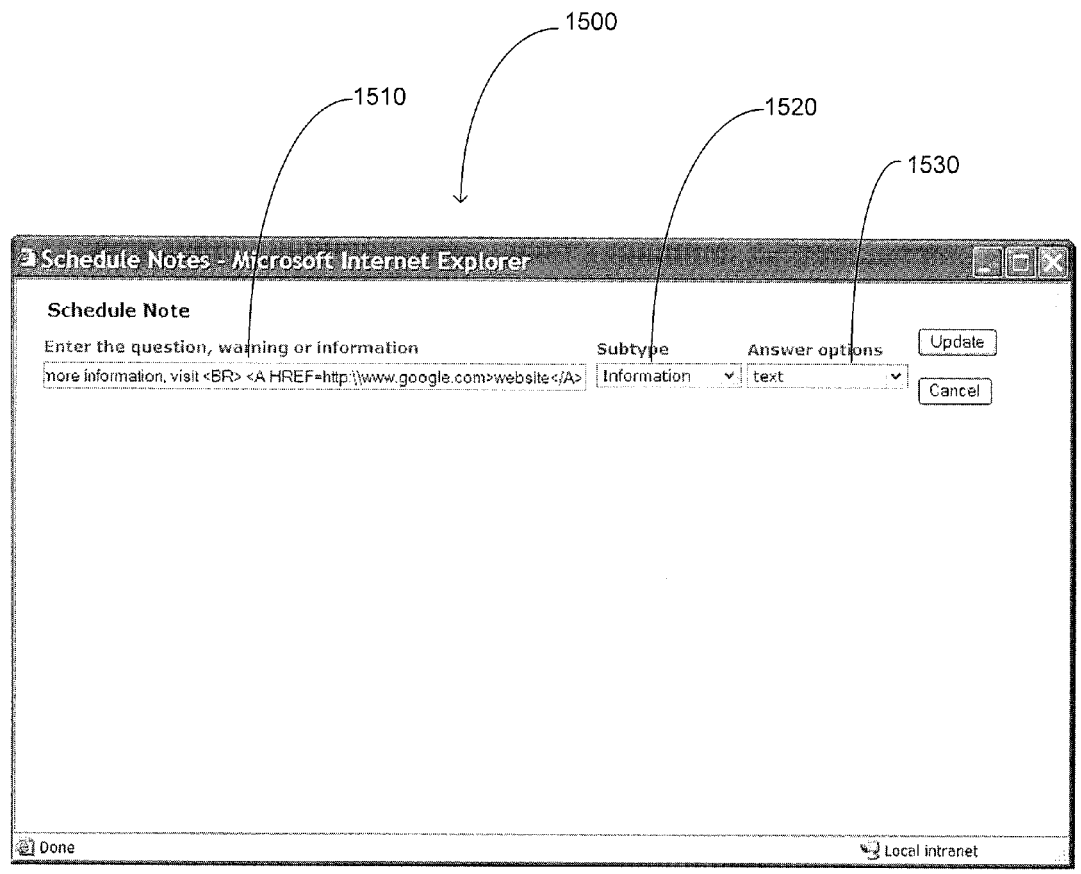
FIG. 15 illustrates one embodiment of a notification window wherein a information notification is in the process of being created.

FIG. 15 is one embodiment of a notification window 1500 wherein a information notification rule is in the process of being created. In the notification text field 1510, and administrator has entered formatted text, which includes HTML code. In particular, the notification text in notification text field 1510 includes a hypertext link to the Google website. Because the notification text 1510 is an information notification, the subtype selected in notification type field 1520 is "information".

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computerized method of scheduling a patient for a medical exam, the method comprising:
   by computing system comprising one or more computing devices:
   generating a dynamically updateable graphical user interface configured to display information to a user, receive inputs from the user, and update the information displayed to the user in response to the inputs received from the user;
   providing, in the user interface, one or more patient information input fields;
   receiving, via the one or more patient information input fields, patient information comprising data identifying a patient;
   determining, based at least in part on information related to the patient, one or more facilities associated with the patient;
   providing, in the user interface, a listing of the one or more facilities associated with the patient;
   receiving, via the user interface, a selection of a facility of the one or more facilities associated with the patient;
   determining, based at least in part on the information related to the specific patient and information related to the facility, one or more exam modalities;
   providing, in the user interface, a listing of the one or more exam modalities in a popup list;
   receiving, via the user interface, a selection of an exam modality of the one or more exam modalities;
   determining, based at least in part on the information related to facility and information related to the exam modality, one or more medical procedures;
   providing, in the user interface, a listing of the one or more medical procedures;
   receiving, via the user interface, a selection of a medical procedure of the one or more medical procedures, wherein information related to the medical procedure, the information related to the exam modality, the information related to the facility, and the information related to the patient collectively comprise exam parameters associated with a medical exam to be scheduled for the patient;
   selecting, from a notification data structure and based at least in part on one or more exam parameters, one or more notifications for display to the user, wherein:
   the notification data structure includes at least:
   indications of exam parameters, notification texts, and notification types, and associations between exam parameters and respective notification text and notification types;

at least one of the one or more notifications comprises a hard question that requires a response from the user before scheduling of the medical exam may be completed; and at least one of the one or more notifications comprises a warning that requires an acknowledgement from the user before scheduling of the medical exam may be completed;

providing, in the user interface, the one or more notifications including the hard question and the warning;

automatically determining whether the hard question has received a response from the user;

automatically determining whether the warning has received an acknowledgement from the user; and in response to determining that the hard question did not receive a response from the user or the warning did not receive an acknowledgement from the user, automatically preventing completion of the exam scheduling.

2. The computerized method of claim 1, wherein the exam parameters comprise indications of at least one of: an exam modality, a medical procedure, a facility, an insurance type, a medical history, a patient age or age category, patient demographics, or a language.

3. The computerized method of claim 1, wherein the user comprises at least one of: the patient, a relative of the patient, a clerical worker, or a scheduling agent.

4. The computerized method of claim 1, wherein at least one of the one or more notifications comprises a soft question that does not require a response or acknowledgement from the user in order to complete scheduling of the medical exam.

5. The computerized method of claim 1, wherein at least one of the one or more notifications comprises an informational notification that does not require a response or acknowledgement from the user in order to complete scheduling of the medical exam.

* * * * *